US008802696B2

(12) United States Patent
Liu et al.

(10) Patent No.: US 8,802,696 B2
(45) Date of Patent: *Aug. 12, 2014

(54) 7-([1,2,4]TRIAZOLO[1,5-A]PYRIDIN-6-YL)-4-(3,4-DICHLOROPHENYL)-1,2,3,4-TETRAHYDROISOQU INOLI AND USE THEREOF

(75) Inventors: Shuang Liu, Schenectady, NY (US); Bruce F. Molino, Slingerlands, NY (US); Kassoum Nacro, Albany, NY (US)

(73) Assignee: Albany Molecular Research, Inc., Albany, NY (US)

( * ) Notice: Subject to any disclaimer, the term of this patent is extended or adjusted under 35 U.S.C. 154(b) by 157 days.

This patent is subject to a terminal disclaimer.

(21) Appl. No.: 12/777,776

(22) Filed: May 11, 2010

(65) Prior Publication Data

US 2010/0292243 A1 Nov. 18, 2010

Related U.S. Application Data

(60) Provisional application No. 61/177,474, filed on May 12, 2009.

(51) Int. Cl.
*C07D 471/04* (2006.01)
*A61K 31/495* (2006.01)

(52) U.S. Cl.
USPC .......................................... 514/303; 546/119

(58) Field of Classification Search
None
See application file for complete search history.

(56) References Cited

U.S. PATENT DOCUMENTS

| | | | |
|---|---|---|---|
| 3,666,763 A | 5/1972 | Grethe et al. |
| 3,947,456 A | 3/1976 | Rheiner |
| 4,113,869 A | 9/1978 | Gardner |
| 4,340,600 A | 7/1982 | Brenner et al. |
| 4,564,613 A | 1/1986 | Boltze et al. |
| 4,843,071 A | 6/1989 | Hohenwarter |
| 4,902,710 A | 2/1990 | Foster et al. |
| 5,212,185 A | 5/1993 | Hanson |
| 5,241,065 A | 8/1993 | Berger et al. |
| 5,444,070 A | 8/1995 | Moldt et al. |
| 5,447,947 A | 9/1995 | Campbell |
| 5,532,244 A | 7/1996 | Wong et al. |
| 5,595,872 A | 1/1997 | Wetterau, II et al. |
| 5,654,296 A | 8/1997 | Kato et al. |
| 5,654,316 A | 8/1997 | Carruthers et al. |
| 5,656,642 A | 8/1997 | Fujioka et al. |
| 5,789,449 A | 8/1998 | Norden |
| 5,817,832 A | 10/1998 | Wallquist et al. |
| 5,827,875 A | 10/1998 | Dickson, Jr. et al. |
| 5,885,983 A | 3/1999 | Biller et al. |
| 6,043,253 A | 3/2000 | Brockunier et al. |
| 6,121,261 A | 9/2000 | Glatt et al. |
| 6,136,803 A | 10/2000 | Freedman et al. |
| 6,162,809 A | 12/2000 | Kohl et al. |
| 6,211,170 B1 | 4/2001 | Yoakim et al. |
| 6,218,404 B1 | 4/2001 | Bigge et al. |
| 6,239,125 B1 | 5/2001 | Malenfant et al. |
| 6,262,074 B1 | 7/2001 | Otten et al. |
| 6,340,681 B1 | 1/2002 | Ito |
| 6,358,993 B1 | 3/2002 | Reddy et al. |
| 6,479,436 B1 | 11/2002 | Otten et al. |
| 6,506,772 B1 | 1/2003 | Brodbeck et al. |
| 6,506,773 B2 | 1/2003 | Hannah et al. |
| 6,562,836 B1 | 5/2003 | Szarek et al. |
| 6,579,885 B2 | 6/2003 | Beck et al. |
| 6,586,447 B1 | 7/2003 | Lyssikatos et al. |
| 6,642,228 B1 | 11/2003 | Hayashi et al. |
| 6,664,293 B2 | 12/2003 | Yamada et al. |
| 6,703,405 B2 | 3/2004 | Hofmeister et al. |
| 6,900,220 B2 | 5/2005 | Becker et al. |
| 6,911,453 B2 | 6/2005 | Hofmeister et al. |
| 6,919,376 B2 | 7/2005 | Llompart et al. |
| 6,943,159 B1 | 9/2005 | Gouliaev et al. |
| 6,974,803 B2 | 12/2005 | Yeadon |
| 6,977,261 B2 | 12/2005 | Bunker et al. |
| 7,041,702 B1 | 5/2006 | Durant et al. |
| 7,084,152 B2 | 8/2006 | Beck et al. |
| 7,163,949 B1 | 1/2007 | Beck et al. |
| 7,211,584 B2 | 5/2007 | Jover et a |
| 7,211,585 B2 | 5/2007 | Jover et a |
| 7,241,774 B2 | 7/2007 | Miller et al. |
| 7,241,775 B2 | 7/2007 | Hofmeister et al. |
| 7,256,201 B2 | 8/2007 | Barlaam et al. |
| 7,265,116 B2 | 9/2007 | Beck et al. |
| 7,268,142 B2 | 9/2007 | Allen et al. |
| 7,309,789 B2 | 12/2007 | Beck et al. |
| 7,345,057 B2 | 3/2008 | Torrens Jover et al. |

(Continued)

FOREIGN PATENT DOCUMENTS

| | | |
|---|---|---|
| CA | 2015114 | 10/1990 |
| CH | 538 477 | 8/1973 |

(Continued)

OTHER PUBLICATIONS

West, Anthony R., Solid State Chemistry and its Applications, Wiley, New York, 1988, pp. 358 & 365.*
Mondeshka et al., "Resolution, Absolute Stereochemistry and Enantiospecificity of 4-(4-bromophenyl)-2- methyl-1,2,3,4-tetrahydroisoquinoline. The Crystal and Molecular Structures of the Racemic and 4R-Enantiomeric Hydrochloride Salt Forms," Acta. Chemica. Scandinavica 48:689-698 (1994).
Office Action dated May 31, 2012 for U.S. Appl. No. 12/777,728.
International Search Report and Written Opinion for International Application No. PCT/US10/34373 dated on Jun. 18, 2010.
International Search Report and Written Opinion for International Application No. PCT/US10/34379 dated on Jun. 21, 2010.

(Continued)

*Primary Examiner* — Zinna Northington Davis
(74) *Attorney, Agent, or Firm* — LeClairRyan, A Professional Corporation

(57) ABSTRACT

Novel [1,2,4]triazolo[1,5-a]pyridinyl-6-yl-substituted tetrahydroisoquinolines are described in the present invention. These compounds and crystalline forms SA1 and N-2 are used in the treatment of various neurological and physiological disorders. Methods of making these compounds and crystalline forms SA-1 and N-2 are also described in the present invention.

8 Claims, 3 Drawing Sheets

(56) References Cited

U.S. PATENT DOCUMENTS

| | | |
|---|---|---|
| 7,388,019 B2 | 6/2008 | Ashton et al. |
| 7,419,985 B2 | 9/2008 | Beck et al. |
| 7,425,633 B2 | 9/2008 | Jiaang et al. |
| 7,459,460 B2 | 12/2008 | Yang et al. |
| 7,491,794 B2 | 2/2009 | Blatt et al. |
| 7,501,538 B2 | 3/2009 | Mjalli et al. |
| 7,541,357 B2 | 6/2009 | Molino et al. |
| 7,544,497 B2 | 6/2009 | Sinclair et al. |
| 7,582,803 B2 | 9/2009 | Akerman et al. |
| 7,612,090 B2 | 11/2009 | Beck et al. |
| 7,790,742 B2 | 9/2010 | Lang et al. |
| 7,846,930 B2 | 12/2010 | Keith |
| 7,872,138 B2 | 1/2011 | Villani et al. |
| 7,973,057 B2 | 7/2011 | Greig et al. |
| 8,178,545 B2 | 5/2012 | Brown |
| 8,227,486 B2 | 7/2012 | Molino et al. |
| 8,236,796 B2 | 8/2012 | Molino et al. |
| 8,420,811 B2 | 4/2013 | Lobben et al. |
| 8,445,494 B2 | 5/2013 | Qiu et al. |
| 2003/0203920 A1 | 10/2003 | Beck et al. |
| 2004/0044000 A1 | 3/2004 | Bunker et al. |
| 2004/0044211 A1 | 3/2004 | Hofmeister et al. |
| 2004/0248932 A1 | 12/2004 | Frail et al. |
| 2004/0248933 A1 | 12/2004 | Frail et al. |
| 2005/0020597 A1 | 1/2005 | Beck et al. |
| 2005/0113283 A1 | 5/2005 | Solow-Cordero et al. |
| 2005/0171027 A1 | 8/2005 | Sinclair et al. |
| 2005/0261298 A1 | 11/2005 | Solow-Cordero et al. |
| 2006/0014705 A1 | 1/2006 | Howitz et al. |
| 2006/0052378 A1 | 3/2006 | Molino et al. |
| 2006/0063766 A1 | 3/2006 | Molino et al. |
| 2006/0084135 A1 | 4/2006 | Howitz et al. |
| 2006/0111385 A1 | 5/2006 | Molino et al. |
| 2006/0111386 A1 | 5/2006 | Molino et al. |
| 2006/0111393 A1 | 5/2006 | Molino et al. |
| 2006/0111394 A1 | 5/2006 | Molino et al. |
| 2006/0111395 A1 | 5/2006 | Molino et al. |
| 2006/0111396 A1 | 5/2006 | Molino et al. |
| 2006/0194837 A1 | 8/2006 | Carruthers et al. |
| 2006/0217409 A1 | 9/2006 | Beck et al. |
| 2006/0229265 A1 | 10/2006 | Milburn et al. |
| 2006/0276416 A1 | 12/2006 | Sinclair et al. |
| 2007/0015737 A1 | 1/2007 | Clark et al. |
| 2007/0048728 A1 | 3/2007 | Ratcliffe et al. |
| 2007/0060589 A1 | 3/2007 | Purandare et al. |
| 2007/0082907 A1 | 4/2007 | Canada et al. |
| 2007/0105838 A1 | 5/2007 | Best et al. |
| 2007/0112012 A1 | 5/2007 | Boehringer et al. |
| 2008/0004336 A1 | 1/2008 | Gougoutas et al. |
| 2008/0207595 A9 | 8/2008 | Molino et al. |
| 2008/0318997 A1 | 12/2008 | Beck et al. |
| 2009/0048443 A1 | 2/2009 | Molino et al. |
| 2009/0069374 A1 | 3/2009 | Skolnick et al. |
| 2009/0099158 A1 | 4/2009 | Grice et al. |
| 2009/0253906 A1 | 10/2009 | Molino et al. |
| 2010/0137278 A1 | 6/2010 | Guzzo et al. |
| 2010/0210624 A1 | 8/2010 | Liu et al. |
| 2010/0292242 A1 | 11/2010 | Liu et al. |
| 2010/0292250 A1 | 11/2010 | Wei et al. |
| 2012/0046271 A1 | 2/2012 | Guzzo et al. |

FOREIGN PATENT DOCUMENTS

| | | |
|---|---|---|
| DE | 2 062 001 | 7/1971 |
| DE | 102005025625 A1 | 12/2006 |
| EP | 0 140 070 A1 | 5/1985 |
| EP | 0 360 390 A1 | 3/1990 |
| EP | 0380223 A1 | 8/1990 |
| EP | 0 394 989 B1 | 10/1990 |
| EP | 0 400 319 A1 | 12/1990 |
| EP | 0421436 A2 | 4/1991 |
| EP | 0 428 434 A2 | 5/1991 |
| EP | 0 429 366 B1 | 5/1991 |
| EP | 0 430 771 B1 | 6/1991 |
| EP | 0 436 334 B1 | 7/1991 |
| EP | 0 443 132 B1 | 8/1991 |
| EP | 0 482 539 B1 | 4/1992 |
| EP | 0 498 069 B1 | 8/1992 |
| EP | 0 499 313 B1 | 8/1992 |
| EP | 0 512 901 B1 | 11/1992 |
| EP | 0 512 902 A1 | 11/1992 |
| EP | 0 514 273 A1 | 11/1992 |
| EP | 0 514 274 A1 | 11/1992 |
| EP | 0 514 275 A1 | 11/1992 |
| EP | 0 514 276 A1 | 11/1992 |
| EP | 0 515 681 A1 | 12/1992 |
| EP | 0 517 589 B1 | 12/1992 |
| EP | 0 520 555 A1 | 12/1992 |
| EP | 0 522 808 A2 | 1/1993 |
| EP | 0 528 495 A1 | 2/1993 |
| EP | 0 532 456 B1 | 3/1993 |
| EP | 0 533 280 B1 | 3/1993 |
| EP | 0 536 817 A1 | 4/1993 |
| EP | 0 545 478 A1 | 6/1993 |
| EP | 0 558 156 A2 | 9/1993 |
| EP | 0 577 394 B1 | 1/1994 |
| EP | 0 585 913 B1 | 3/1994 |
| EP | 0 599 338 A2 | 6/1994 |
| EP | 0599538 A1 | 6/1994 |
| EP | 0 610 793 A1 | 8/1994 |
| EP | 0 634 402 A1 | 1/1995 |
| EP | 0 686 629 A2 | 12/1995 |
| EP | 0 693 489 A1 | 1/1996 |
| EP | 0 694 535 A1 | 1/1996 |
| EP | 0 699 674 A1 | 3/1996 |
| EP | 0 707 006 B1 | 4/1996 |
| EP | 0 708 101 B1 | 4/1996 |
| EP | 0 709 375 A2 | 5/1996 |
| EP | 0 709 376 A2 | 5/1996 |
| EP | 0 714 891 A1 | 6/1996 |
| EP | 0 723 959 A1 | 7/1996 |
| EP | 0 733 632 A1 | 9/1996 |
| EP | 0 776 893 A1 | 6/1997 |
| EP | 0 699 655 B1 | 9/1997 |
| EP | 0 520 555 B1 | 9/1999 |
| GB | 2 266 529 A | 11/1993 |
| GB | 2 268 931 A | 1/1994 |
| GB | 2 269 170 A | 2/1994 |
| GB | 2 269 590 A | 2/1994 |
| GB | 2 271 566 A | 4/1994 |
| GB | 2 271 774 A | 4/1994 |
| GB | 2 292 144 A | 2/1996 |
| GB | 2 293 168 A | 3/1996 |
| GB | 2 293 169 A | 3/1996 |
| GB | 2 302 689 A | 1/1997 |
| HU | 9903186 A2 | 2/2000 |
| JP | 52-23083 A | 2/1977 |
| JP | 2002281203 A | 11/1990 |
| JP | 04193867 | 7/1992 |
| JP | 10-292008 | 11/1998 |
| JP | 2000086110 A | 7/2000 |
| JP | 2001026580 A | 1/2001 |
| JP | 2003513074 A | 4/2003 |
| JP | 2004501860 A | 1/2004 |
| WO | WO 90/05525 | 5/1990 |
| WO | WO 90/05729 | 5/1990 |
| WO | WO 91/09844 | 7/1991 |
| WO | WO 91/18899 | 12/1991 |
| WO | WO 92/01688 | 2/1992 |
| WO | WO 92/06079 | 4/1992 |
| WO | WO 92/12151 | 7/1992 |
| WO | WO 92/15585 | 9/1992 |
| WO | WO 92/17449 | 10/1992 |
| WO | WO 92/20661 | 11/1992 |
| WO | WO 92/20676 | 11/1992 |
| WO | WO 92/21677 | 12/1992 |
| WO | WO 92/22569 | 12/1992 |
| WO | WO 93/00330 | 1/1993 |
| WO | WO 93/00331 | 1/1993 |
| WO | WO 93/01159 | 1/1993 |
| WO | WO 93/01165 | 1/1993 |
| WO | WO 93/01169 | 1/1993 |
| WO | WO 93/01170 | 1/1993 |

(56) References Cited

FOREIGN PATENT DOCUMENTS

| | | |
|---|---|---|
| WO | WO 93/06099 | 4/1993 |
| WO | WO 93/09116 | 5/1993 |
| WO | WO 93/10073 | 5/1993 |
| WO | WO 93/14084 | 7/1993 |
| WO | WO 93/14113 | 7/1993 |
| WO | WO 93/18023 | 9/1993 |
| WO | WO 93/19064 | 9/1993 |
| WO | WO 93/21155 | 10/1993 |
| WO | WO 93/21181 | 10/1993 |
| WO | WO 93/23380 | 11/1993 |
| WO | WO 93/24465 | 12/1993 |
| WO | WO 94/00440 | 1/1994 |
| WO | WO 94/01402 | 1/1994 |
| WO | WO 94/02461 | 2/1994 |
| WO | WO 94/02595 | 2/1994 |
| WO | WO 94/03429 | 2/1994 |
| WO | WO 94/03445 | 2/1994 |
| WO | WO 94/04494 | 3/1994 |
| WO | WO 94/04496 | 3/1994 |
| WO | WO 94/05625 | 3/1994 |
| WO | WO 94/07843 | 4/1994 |
| WO | WO 94/08997 | 4/1994 |
| WO | WO 94/10165 | 5/1994 |
| WO | WO 94/10167 | 5/1994 |
| WO | WO 94/10168 | 5/1994 |
| WO | WO 94/10170 | 5/1994 |
| WO | WO 94/11368 | 5/1994 |
| WO | WO 94/13639 | 6/1994 |
| WO | WO 94/13663 | 6/1994 |
| WO | WO 94/14767 | 7/1994 |
| WO | WO 94/15903 | 7/1994 |
| WO | WO 94/19320 | 9/1994 |
| WO | WO 94/19323 | 9/1994 |
| WO | WO 94/20500 | 9/1994 |
| WO | WO 94/26735 | 11/1994 |
| WO | WO 94/26740 | 11/1994 |
| WO | WO 94/29309 | 12/1994 |
| WO | WO 95/02595 | 1/1995 |
| WO | WO 95/04040 | 2/1995 |
| WO | WO 95/04042 | 2/1995 |
| WO | WO 95/06645 | 3/1995 |
| WO | WO 95/07886 | 3/1995 |
| WO | WO 95/07908 | 3/1995 |
| WO | WO 95/08549 | 3/1995 |
| WO | WO 95/11880 | 5/1995 |
| WO | WO 95/14017 | 5/1995 |
| WO | WO 95/15311 | 6/1995 |
| WO | WO 95/16679 | 6/1995 |
| WO | WO 95/17382 | 6/1995 |
| WO | WO 95/18124 | 7/1995 |
| WO | WO 95/18129 | 7/1995 |
| WO | WO 95/20575 | 8/1995 |
| WO | WO 95/21819 | 8/1995 |
| WO | WO 95/22525 | 8/1995 |
| WO | WO 95/23798 | 9/1995 |
| WO | WO 95/26338 | 10/1995 |
| WO | WO 95/28418 | 10/1995 |
| WO | WO 95/30674 | 11/1995 |
| WO | WO 95/30687 | 11/1995 |
| WO | WO 95/33744 | 12/1995 |
| WO | WO 96/05181 | 2/1996 |
| WO | WO 96/05193 | 2/1996 |
| WO | WO 96/05203 | 2/1996 |
| WO | WO 96/06094 | 2/1996 |
| WO | WO 96/07649 | 3/1996 |
| WO | WO 96/10562 | 4/1996 |
| WO | WO 96/16939 | 6/1996 |
| WO | WO 96/18643 | 6/1996 |
| WO | WO 96/20197 | 7/1996 |
| WO | WO 96/21661 | 7/1996 |
| WO | WO 96/29304 | 9/1996 |
| WO | WO 96/29317 | 9/1996 |
| WO | WO 96/29326 | 9/1996 |
| WO | WO 96/29328 | 9/1996 |
| WO | WO 96/31214 | 10/1996 |
| WO | WO 96/32385 | 10/1996 |
| WO | WO 96/37489 | 11/1996 |
| WO | WO 97/01553 | 1/1997 |
| WO | WO 97/01554 | 1/1997 |
| WO | WO 97/03066 | 1/1997 |
| WO | WO 97/08144 | 3/1997 |
| WO | WO 97/14671 | 4/1997 |
| WO | WO 97/17362 | 5/1997 |
| WO | WO 97/18206 | 5/1997 |
| WO | WO 97/19084 | 5/1997 |
| WO | WO 97/19942 | 6/1997 |
| WO | WO 97/21702 | 6/1997 |
| WO | WO 97/23458 | 7/1997 |
| WO | WO 97/36876 | 10/1997 |
| WO | 1997043255 A1 | 11/1997 |
| WO | 1997043257 A1 | 11/1997 |
| WO | WO 97/49710 | 12/1997 |
| WO | 1998035939 A1 | 8/1998 |
| WO | WO 98/40358 | 9/1998 |
| WO | 2000014076 A1 | 3/2000 |
| WO | 2001032625 A1 | 5/2001 |
| WO | WO 01/32624 A1 | 5/2001 |
| WO | 2001070728 A1 | 9/2001 |
| WO | WO 02/04455 A2 | 1/2002 |
| WO | 2003077874 A2 | 9/2003 |
| WO | 2004067514 A1 | 8/2004 |
| WO | 2004096774 A1 | 11/2004 |
| WO | 2005035503 A1 | 4/2005 |
| WO | 2005087235 A1 | 9/2005 |
| WO | 2005095403 A2 | 10/2005 |
| WO | 2006020049 A2 | 2/2006 |
| WO | 2006020145 A2 | 2/2006 |
| WO | 2006/057955 A2 | 6/2006 |
| WO | 2006087309 A1 | 8/2006 |
| WO | 2007038459 A2 | 4/2007 |
| WO | 2007048788 A1 | 5/2007 |
| WO | 2007098608 A1 | 9/2007 |
| WO | 2007117982 A2 | 10/2007 |
| WO | 2008024398 A2 | 2/2008 |
| WO | 2008037482 A1 | 4/2008 |
| WO | 2009/155565 A1 | 12/2009 |
| WO | 2010/027500 A1 | 3/2010 |
| WO | 2010132437 A1 | 11/2010 |
| WO | 2010132442 A1 | 11/2010 |
| WO | 2010132487 A1 | 11/2010 |

OTHER PUBLICATIONS

International Search Report and Written Opinion for International Application No. PCT/US10/34428 dated on Jun. 21, 2010.
European Search Report dated Nov. 2, 2012, for EP Application Serial No. 10775394.9.
European Search Report dated Dec. 7, 2012, for EP Application No. 10775398.0.
European Search Report dated Jan. 2, 2013, for EP Application No. 10775425.1.
Office Action dated Nov. 13, 2012, for U.S. Appl. No. 12/777,840.
Office Action dated Jan. 4, 2013 for China Patent Application No. 200580030990.2.
Substantive Examination Report and Search Report dated Apr. 15, 2011 for Malaysian Patent Application No. PI20070018.
Opposition dated Jan. 22, 2013 for Chilean Patent Application No. 2810-2011 (redacted).
Search Report and Written Opinion dated Jan. 11, 2013 for Singapore Patent Application No. 201108011-6.
Office Action dated Oct. 6, 2011 for Singapore Patent Application No. 200904617-8.
Office Action dated Dec. 16, 2011 for China Patent Application No. 200580030990.2.
Office Action dated Oct. 28, 2011 for U.S. Appl. No. 12/417,598.
International Search Report and Written Opinion for PCT/US2005/025193 (mailed Aug. 3, 2006).
Office Action dated Jan. 25, 2012 for U.S. Appl. No. 12/252,823.
Translation of Office Action for Colombia Patent Application No. 07 014.254 (received Mar. 20, 2012).
Office Action dated Feb. 14, 2012 for EP 05793999.3.
Translation of Office Action dated Jun. 21, 2012 for Korea Patent Application No. 10-2007-7003549.

(56) References Cited

OTHER PUBLICATIONS

Translation of Office Action dated Jul. 27, 2012 for China Patent Application No. 200580030990.2.
Office Action dated Jul. 27, 2012 for India Patent Application No. 660/CHENP/2007.
Office Action dated Sep. 19, 2012 for EP 05793999.3.
Office Action dated Mar. 5, 2013 for China Patent Application No. 201080031666.3.
Office Action dated Mar. 26, 2013 for Canadian Patent Application No. 2,573,271.
Translation of Office Action for Korean Patent Application No. 10-2013-7001614 (May 16, 2013).
Examination Report for European Patent Application No. 05793999.3 (Apr. 15, 2013).
Examination Report for New Zealand Patent Application No. 596104 (Sep. 13, 2012).
Translation of Office Action for Chinese Patent Application No. 201080031616.5 (May 2, 2013).
Translation of Office Action for Chinese Patent Application No. 200580030990.2 (Jul. 1, 2013).
Hearing Notice in Reference of India Patent Application No. 660/CHENP/2007 dated Jul. 9, 2013.
Translation of Office Action for Eurasian Patent Application No. 201171393 (Mar. 20, 2013).
Aihara et al., "Increasing 5-Lipoxygenase Inhibitory Activities by Oxidative Conversion of o-Methoxyphenols to Catechols Using a $Cu^{2+}$-Ascorbic Acid-$O_2$ System," *Chem. Pharm. Bull.* 38(3):842-844 (1990).
Banerji et al., "Studies on Single-Electron Transfer Reagents. Part IV Reaction of Nitrogen Heterocycles with Sodium Naphthalenide," *Tetrahedron* 50(30):9079-9096 (1994).
Beilstein No. 4048047 (CAS 17074-38-3, 17074-39-4), Beilstein Data, Elsevier Information Systems GmbH, 2 pages (Mar. 19, 1991).
Beilstein No. 4102323 (CAS 53885-34-0), Beilstein Data, Elsevier Information Systems GmbH, 3 pages (Mar. 19, 1991).
Beilstein No. 4341479 (CAS 134021-24-2), Beilstein Data, Elsevier Information Systems GmbH, 5 pages (Jul. 20, 1992).
Beilstein No. 4494373 (CAS 82416-61-3), Beilstein Data, Elsevier Information Systems GmbH, 3 pages (Dec. 2, 1991).
Beilstein No. 455853 (CAS 71730-66-0), Beilstein Data, Elsevier Information Systems GmbH, 2 pages (Nov. 28, 1988).
Beilstein No. 4774688 (CAS 133160-36-8), Beilstein Data, Elsevier Information Systems GmbH, 2 pages (Jul. 20, 1992).
Beilstein No. 4787749 (CAS 133043-12-6, 133160-34-6, 133160-35-7), Beilstein Data, Elsevier Information Systems GmbH, 5 pages (Jul. 20, 1992).
Beilstein No. 4787750 (CAS 133043-12-6, 133160-34-6, 133160-35-7), Beilstein Data, Elsevier Information Systems GmbH, 5 pages (Jul. 20, 1992).
Beilstein No. 4787836 (CAS 133043-20-6, 133043-31-9), Beilstein Data, Elsevier Information Systems GmbH, 4 pages (Jul. 20, 1992).
Beilstein No. 4787837 (CAS 133043-20-6, 133043-31-9), Beilstein Data, Elsevier Information Systems GmbH, 4 pages (Jul. 20, 1992).
Beilstein No. 4788234 (CAS 133043-19-3, 133043-30-8), Beilstein Data, Elsevier Information Systems GmbH, 4 pages (Jul. 20, 1992).
Beilstein No. 4788235 (CAS 133043-19-3, 133043-30-8), Beilstein Data, Elsevier Information Systems GmbH, 4 pages (Jul. 20, 1992).
Beilstein No. 4789758 (CAS 133043-21-7, 133043-22-8), Beilstein Data, Elsevier Information Systems GmbH, 5 pages (Jul. 20, 1992).
Beilstein No. 594629 (CAS 53885-32-8), Beilstein Data, Elsevier Information Systems GmbH, 2 pages (Nov. 28, 1988).
Berge et al., "Pharmaceutical Salts," *J. Pharm. Sci.* 66(1):1-19 (1977).
Blomberg et al., "The Barbier Reaction—A One Step Alternative for Syntheses via Organomagnesium Compounds," *Synthesis* pp. 18-30 (1977).
Bobowski & Gottlieb, "4-Substituted 1,2,3,4-tetrahydro-3,3-dimethylisoquinolines. II.," *J. Heterocyclic Chem.* 19(1):21-27 (1982).
Brown & Dyke, "1,2-Dihydroisoquinolines. II. Berbine Synthesis," *Tetrahedron* 22(8):2429-35 (1966).
Brown & Dyke, "1,2-Dihydroisoquinolines. III. Dimerization," *Tetrahedron* 22(8):2437-2443 (1966).
Bundgaard, "Means to Enhance Penetration," *Adv. Drug Delivery Rev.* 8:1-38 (1992).
Burrows et al., "Antidepressant Efficacy and Tolerability of the Selective Norepinephrine Reuptake Inhibitor Reboxetine: A Review," *J. Clin. Psychiatry* 59(Suppl. 14):4-7 (1998) (98819-76-2 REGISTRY (Reboxetine)).
Bundgaard, *Design of Prodrugs*, Amsterdam, The Netherlands: Elsevier Science Publishers B.V. (1985) (Table of Contents only).
CAS No. 53885-23-7, ACS on STN, 1 page (Nov. 16, 1984).
CAS No. 53885-32-8, ACS on STN, 1 page (Nov. 16, 1984).
Chandrasekhar et al., "Highly Efficient Synthesis of 3-alkyl/aryl-4-aryl-1,2,3,4-tetrahydroisoquinolines from N,N-dibenzylaminols," *Tetrahedron Lett.* 43(10):1885-1888 (2002).
Cherpillod et al., "A Controlled Trial with Diclofensine, A New Psychoactive Drug, in the Treatment of Depression," *J. Int. Med. Res.* 9(5):324-329 (1981).
Cliffe et al., "(S)-N-tert-Butyl-3-(4-(2-methoxyphenyl)-piperazin-1-yl)-2-phenylpropanamide [(S)-WAY-100135]: A Selective Antagonist at Presynaptic and Postsynaptic-5-$HT_{1A}$ Receptors," *J. Med. Chem.* 36:1509-10 (1993).
Dandridge et al., "Synthesis, Resolution, Absolute Stereochemistry, and Enantioselectivity of 3', 4'-Dihydroxynomifensine," *J. Med. Chem.* 27:28-35 (1984).
Desai et al., "Relationship Between in Vivo Occupancy at the Dopamine Transporter and Behavioral Effects of Cocaine, GBR 12909 [1-{2-[Bis-(4-fluorophenyl)methoxy]ethyl}-4-(3-phenylpropyl)piperazine], and Benztropine Analogs," *J. Pharmacol. Exp. Ther.* 315(1):397-404 (2005).
Dudley et al., "The Actions of Xylamine on Central Noradrenergic Neurons," *J. Pharm. Exp. Ther.* 217(3):834-840 (1981).
Euerby et al., "Methylthio Activiating Groups in the Synthesis of Tetrahydroisoquinolines and Tetrahydro-2-benzazepines from N-Allyl- and N-Cinnamyl-benzylamines," J. Chem. Research pp. 40-41 (1987).
Gao et al., "Asymmetric Hetero Diels-Alder Reaction Catalyzed by Stable and Easily Prepared CAB Catalysts," *Tetrahedron* 50(4):979-988 (1994).
Georgiadis et al., "Synthesis and Complexation Properties of a Water-Soluble Optically Active Cyclophane Incorporating a 4-Naphthyl-1,2,3,4-tetrahydroisoquinoline Unit as a Chiral Spacer," *J. Org. Chem.* 56(10):3362-3369 (1991).
Greene et al., *Protective Groups in Organic Synthesis*, 2d. Ed., New York, New York: John Wiley & Sons, Inc. (1991) (Table of Contents only).
Hudlicky, "Fluorination with Diethylaminosulfur Trifluoride and Related Aminofluorosulfuranes," *Organic Reactions* 35:513-637 (1985).
Hyttel, "Pharmacological Characterization of Selective Serotonin Reuptake Inhibitors (SSRIs)," *Int. Clin. Psychopharmacol.* 9(Suppl. 1):19-26 (1994) (6186908-7 REGISTRY (Paroxetine); 59729-32-7 REGISTRY (Citalopram); 79559-97-0 REGISTRY (Sertraline); 54910-89-3 REGISTRY (Fluoxetine); 54739-18-3 REGISTRY (Fluvoxamine)).
Ishikura et al., "The Synthesis of 4-Substituted Isoquinoline Derivatives from Diethyl (4-Isoquinolyl) Borane," *Heterocycles* 26:1603-1610 (1987).
Jacob et al., "Dopamine Agonist Properties of N-Alkyl-4-(3,4-dihydroxyphenyl)-1,2,3,4-tetrahydroisoquinolines," *J. Med. Chem.* 24:1013-1015 (1981).
Jorgenson, "Preparation of Ketones from the Reaction of Organolithium Reagents with Carboxylic Acids," Dauben et al., eds., *Organic Reactions*, vol. 18, New York, New York: John Wiley & Sons, Inc., Chapter 1 (1970) (Table of Contents only).
Kakeya et al., "Studies on Prodrugs of Cephalosporins. I. Synthesis and Biological Properties of Glycyloxybenzoyloxymethyl and Glycylaminobenzoyloxymethyl Esters of 7β[2-(2-Aminothiazol-4-yl)-(Z)-2-Methoxyiminoacetamido]-3-Methyl-3-Cephem-4-Carboxylic Acid," Chem. Pharm. Bull. 32(2):692-698 (1984).

(56) References Cited

OTHER PUBLICATIONS

Kametani et al., "Studies on the Synthesis of Heterocyclic Compounds," *Tetrahedron* 31:235-238 (1975).
Kihara et al., "A Convenient Synthesis of 4-Substituted 1,2,3,4-Tetrahydroisoquinolin-4-OLS by a Novel Intramolecular Barbier Reaction and by an Insertion Reaction: Reaction Scope and Limitations," *Tetrahedron* 48(1):67-78 (1992).
Kihara et al., "Synthesis and Enantioselectivity of Optically Active 1- and 3-Substituted 4-Phenyl-1,2,3,4-Tetrahydroisoquinolin-4-ols and Related Compounds As Norepinephrine Potentiators," *Chem. Pharm. Bull.* 43(9):1543-1546 (1995).
Kihara et al., "Synthesis and Pharmacological Evaluation of Phenolic 2-Methyl-4-Phenyl-1,2,3,4,-Tetrahydroisoquinolin-4-ols As New Norepinephrine Potentiator," *Drug Design Dis.* 11(3):175-183 (1994).
Knabe & Herbort, "Dehydrogenation of Tertiary Amines with Aercury (II) Acetate in the Presence of EDTA. XIII. Oxidative Dimerization of 6,7-dimethoxy-2-methyl-1,1-diethyl-1,2,3,4-tetrahydroisoquinoline," *Archiv. der Pharmazie. und Berichte der Deutschen Pharmazeutischen Gesellschaft* 300(9):774-783 (1967).
Knabe & Renz, "Synthesis of 3,4'-Biisoquinolines," *Archiv. der Pharmazie.* (Weinheim, Germany) 307(8):612-622 (1974) (abstract in English).
Krogsgaard-Larsen et al., eds., *A Textbook of Drug Design and Development*, Chur, Switzerland: Harwood Academic Publishers GmbH (1991) (portion of Table of Contents only).
Larock, *Comprehensive Organic Transformations: A Guide to Functional Group Preparation*, New York, New York: VCH Publishers, Inc. (1989) (Table of Contents only).
Maryanoff et al., "Pyrroloisoquinoline Antidepressants. 2. In-Depth Exploration of Structure-Activity Relationships," *J. Med. Chem.* 30(8):1433-1454 (1987).
McOmie, ed., *Protective Groups in Organic Chemistry*, London: Plenum Press (1973) (Table of Contents only).
Middlemiss et al., "Centrally Active 5-HT Receptor Agonists and Antagonists," *Neurosci. Biobehavioral Rev.* 16:75-82 (1992).
Miller et al., "An Efficient Synthesis of 4-Aryl-1,2,3,4-Tetrahydroisoquinolines," *Synthetic Com.* 24(8):1187-1193 (1994).
Mondeshka et al., "Synthesis, Antiulcer and Antidepressive Activity of 4-(4-Halophenyl)-2-Phenyl-1,2,3,4-Tetrahydroisoquinolines," *Il Farmaco* 49:475-480 (1994).
Müller, "Current St. John's Wort Research from Mode of Action to Clinical Efficacy," *Pharmacological Research* 47:101-109 (2003).
Nielsen et al., "Glycolamide Esters as Biolabile Prodrugs of Carboxylic Acid Agents: Synthesis, Stability, Bioconversion, and Physicochemical Properties," *J. Pharm. Sci.* 77(4):285-298 (1988).
Salama et al., "Antigenic Determinants Responsible for the Reactions of Drug-Dependent Antibodies with Blood Cells," *Br. J. Haematol.* 78:535-539 (1991).
Seebach et al., "Alkylation of Amino Acids without Loss of the Optical Activity: Preparation of α-Substituted Proline Derivatives. A Case of Self-Reproduction of Chirality," *J. American Chem. Soc.* 105(16):5390-5398 (1983).
Stille, "Zur pharmakologischen Prufung von Antidepressiva am Beispiel eines Dibenzodiazepins," *Arzneimittel-Forschung* 14:534-537 (1964) (English summary included on p. 537).
Sugiura & Hamada, "Studies on Nitrogen-Containing Heterocyclic Compounds. XXXV. Syntheses and Reduction of 4-Amino-2-cyano-1,3-dimethoxy-1,2,3,4-tetrahydroisoquinolines," *Yakugaku Zasshi* 99(6):556-563 (1979).
Sugiura et al., "Synthesis and Stereochemistry of 3,7-Diazatricyclo[4.2.2.2$^{2,5}$]dodeca-9,11-dienes Derived by [4+4] Cyclodimerization of 2,3-Dihydroisoquinoline Derivatives," *Chem. Pharm. Bull.* 46(12):1862-1865 (1998).
Tirelli et al., "Differential Effects of Direct and Indirect Dopamine Agonists on the Induction of Gnawing in C57Bl/6J Mice," *J Pharm. Exp. Therapy* 273(1):7-15 (1995).
Trepanier et al., "3,4-Dihydroisocarbostyril and 1,2,3,4-Tetrahydroisoquinoline Derivatives of Ephedrine," *J. Med. Chem.* 16(4):342-347 (1973).
Uno & Okada, "A Novel Method for the Synthesis of 4-Isoquinolinols," *J. Heterocyclic Chem.* 28(2):341-346 (1991).
Venkov et al., "A New Synthesis of 1,2,3,4-Tetrahydro-2-Methyl-4-Phenylisoquinolines," *Synthesis* 253-255 (1990).
Zára-Kaczián et al., "8-Amino-4-Aryl-2Methyl-1,2,3,4-Tetrahydroisoquinlines: Reactions of the Amino Group Via the Diazonium Salts," *Acta Chimica Hungarica*, 12(4):573-584 (1989).
Office Action dated Jun. 16, 2011 for JP 2007-521686.
Office Action dated Aug. 20, 2010 for AU 2005274927.
Office Action dated Sep. 18, 2009 for CH 200580030990.2.
Supplemental Search Report dated Jul. 9, 2010 for EP 05793999.3.
Office Action dated Oct. 18, 2010 for IL 180349.
Office Action dated Mar. 18, 2011 for SI 200904617-8.
Office Action dated Mar. 5, 2009 for RU 2007105596.
Office Action dated Aug. 24, 2009 for RU 2007105596.
Office Action dated Apr. 10, 2008 for SI 2007001670.
Translation of Office Action for Chinese Patent Application No. 201080031666.3 (Jan. 15, 2014).
Office Action dated Jun. 5, 2013 for China Patent Application No. 201080031617.X.
Translation of Office Action for Thai Patent Application No. 1101003072 (Sep. 18, 2013) (redacted).
Translation of Office Action for Mexico Patent Application No. MX/a/2011/011900 (Sep. 17, 2013) (redacted).
Examination report for European Patent Application No. 10775398.0 (Aug. 13, 2013).
Office Action dated Aug. 29, 2013 for Korean Patent Application No. 10-2007-7003549 (redacted).
Translation of Official Action for Mexican Patent Application No. MX/a/2009/012414 (Oct. 16, 2013) (redacted).
Translation of Notice of Reasons for Rejection for Japanese Patent Application No. 2012-086151 (Oct. 11, 2013).
Written Opinion for Singapore Application No. 201108011-6 (mailed Aug. 9, 2013).
Translation of Official Action for Mexican Patent Application No. MX/a/2011/011901 (Sep. 19, 2013) (redacted).
Examination report for European Patent Application No. 05793999.3 (Oct. 16, 2013).
Examination report for Philippines Patent Application No. 1/2010/501539 (Oct. 8, 2013) (redacted).
Office Action dated Jun. 23, 2008 for U.S. Appl. No. 11/183,066.
Translation of Office Action dated Oct. 23, 2013 for Eurasian Patent Application No. 201171393 (redacted).
Translation of Office Action dated Mar. 31, 2014 for Chile Patent Application No. 2810-2011 (redacted).
Translation of Notice of Defects dated Apr. 2, 2014 for Israel Patent Application No. 216049 (redacted).
Office Action for U.S. Appl. No. 12/777,728 (Apr. 7, 2014).
Banker et al., "Modern Pharmaceutics," 3rd Ed., p. 451, 596 (1996).
"Burger's Medicinal Chemistry and Drug Discovery" edited by Manfred E. Wolff, 5th Ed. Part 1, pp. 975-977 (1995).
Vippagunta et al., "Crystalline Solids," Adv. Drug Del. Rev. 48:3-26 (2001).
Office Action dated Mar. 25, 2014 for Canadian Patent Application No. 2,573,271.
Translation of Office Action dated Mar. 18, 2014 for Mexican Patent Application No. MX/a/2011/011900 (redacted).
Translation of Office Action dated Mar. 12, 2014 for Taiwan Patent Application No. 099115160.
Translation of Office Action dated Mar. 11, 2014 for China Patent Application No. 201080031616.5.
Office Action for Japanese Patent Application No. 2012-510933 dated Jun. 25, 2014.
Translation of Office Action for Chinese Patent Application No. 201080031617.X dated Apr. 24, 2014.
Office Action for Japanese Patent Application No. 2012-510930 dated Jun. 25, 2014.

\* cited by examiner

7-([1,2,4]TRIAZOLO[1,5-A]PYRIDIN-6-YL)-4-(3,4-DICHLOROPHENYL)-1,2,3,4-TETRAHYDROISOQU INOLI AND USE THEREOF

This application claims the benefit of U.S. Provisional Patent Application Ser. No. 61/177,474, filed May 12, 2009, which is hereby incorporated by reference in its entirety.

FIELD OF THE INVENTION

The present invention relates to compounds, crystalline forms, compositions, and methods for the treatment of various neurological and psychological disorders, and the use of the compounds and crystalline forms in combination therapy. In particular, the present invention relates to such compounds, crystalline forms, compositions, and methods, where the compounds are novel [1,2,4]triazolo[1,5-a]pyridinyl-6-yl-substituted tetrahydroisoquinoline derivatives. Methods of making these compounds and crystalline forms SA-1 and N-2 are also described in the present invention.

BACKGROUND OF THE INVENTION

Monoamine reuptake inhibitors elevate extracellular levels of serotonin (5-HT), norepinephrine (NE) and/or dopamine (DA) in the brain by binding to one or more of the transporters responsible for reuptake, namely the serotonin transporter (SERT), the norepinephrine transporter (NET) and the dopamine transporter (DAT), thereby blocking reuptake of the neurotransmitter(s) from the synaptic cleft. Monoamine reuptake inhibitors are an established drug class that has proven utility for the treatment of a number of CNS disorders especially major depressive disorder (MDD).

Since the introduction of tricylic antidepressants (TCAs) almost 50 years ago, monoamine reuptake inhibitors with greatly improved safety profiles have significantly enhanced the treatment of depression. Although TCAs are very effective antidepressants, cardiovascular, anticholinergic and sedative side effects are common due to the interaction of TCAs with muscarinic, histaminic and adrenergic receptors. The revolutionary introduction of selective serotonin reuptake inhibitors (SSRIs) in the 1980s allowed a much larger patient population to be treated because of the highly improved safety profile. Over the past decades, inhibitors that selectively block the reuptake of NE or DA, or two of the three neurotransmitters simultaneously, have become available for the treatment of CNS disorders including depression, anxiety, obsessive compulsive disorder (OCD), attention deficit hyperactivity disorder (ADHD), pain and urinary incontinence. Two representative recent reviews (Liu and Molino, *Annual Reports in Medicinal Chemistry*, 42:13 (2007); Walter, *Drug Dev. Res.*, 65:97 (2005)) on monoamine reuptake inhibitors summarized the history and recent development in the monoamine reuptake inhibitor area.

Currently, the major effort in the field of monoamine reuptake inhibitors is focused on improving antidepressant efficacy since 30-40% of patients do not respond to treatment with currently available antidepressants. An additional major objective is to enhance the onset of action. Current antidepressants typically require 2-6 weeks of treatment before clinical efficacy is seen. Clinical trials exploring augmentation strategies, in which a DA reuptake inhibitor or a dual NE/DA reuptake inhibitor is combined with an SSRI, have resulted in improved efficacy in depressed patients refractory to SSRI treatment alone (Patkar et. al, *J. Clin. Psychopharmacol.*, 26:653 (2006); Zisook et al, *Biol. Psychiat.*, 59:203 (2006)). The improved results from clinical trials such as these serve to justify the considerable focus on the development of inhibitors that simultaneously block the reuptake of 5-HT, NE and DA. Because of the continued need for better drugs to treat depression and the opportunities for new clinical indications, efforts to discover novel monoamine reuptake inhibitors continue unabated.

Methylphenidate, currently used for the treatment of attention deficit-hyperactivity disorder, is known to be selective for inhibition of the DAT. Also, U.S. Pat. No. 5,444,070 discloses selective inhibitors of dopamine reuptake as treatments for Parkinson's disease, drug addiction or abuse including cocaine and amphetamines.

Selective norepinephrine reuptake inhibitors (NARI) have also been disclosed. U.S. Pat. No. 6,352,986 describes methods of treating attention deficit-hyperactivity disorder (ADHD), addictive disorders, and psychoactive substance use disorders with Reboxetine. Also, Atomoxetine (STRATTERA®) is currently marketed as a selective NET reuptake inhibitor for ADHD.

The use of selective serotonin reuptake inhibitors (SSRI) has been shown to be effective in treating depressive disorders. Sertraline, citalopram, escitalopram, paroxetine, fluoxetine and fluvoxamine are well known examples of SSRIs used to treat disorders such as depression, obsessive compulsive disorder, and panic attacks. There are several known difficulties with the SSRI class of therapeutics, including the slow onset of action, unwanted side effects, and the existence of a significant subset of the population that is not responsive to SSRI therapy. Recent effort in the clinical development of new SSRIs has focused on the treatment of premature ejaculation (PE) by taking advantage of the ejaculation-delaying side effects of SSRIs. Although SSRIs have been prescribed off-label to treat this condition, an SSRI with rapid onset of action and rapid clearance could be preferred for on-demand treatment of PE. Dapoxetine (LY210448, 6), an SSRI structurally related to fluoxetine with a shorter half-life, was reported to be an effective and generally well tolerated treatment for men with moderate-to-severe PE in clinical trials (Feret, *Formulary*, 40:227 (2005); Pryor et al, *Lancet*, 368: 929 (2006)).

Selective inhibitors of DAT, NET, and SERT reuptake may also be co-administered with each other or with other drugs. U.S. Pat. No. 5,532,244 discloses the use of serotonin reuptake inhibitors in combination with a serotonin 1A antagonist for the treatment of obsessive-compulsive disorder, depression, and obesity. The use of a serotonin or norepinephrine reuptake inhibitor in combination with a neurokinin-1 receptor antagonist has been disclosed in U.S. Pat. No. 6,121,261 for the treatment of ADHD. U.S. Pat. No. 4,843,071 discloses the use of a norepinephrine reuptake inhibitor in combination with a norepinephrine precursor in the treatment of obesity, drug abuse, or narcolepsy. U.S. Pat. No. 6,596,741 discloses the use of a NE, DA, or 5-HT inhibitor with either a neurokinin-1 receptor antagonist or a serotonin-1A antagonist for the treatment of a wide variety of conditions.

Also advantageous is the use of compounds that inhibit one or more of the neurotransmitters at the same time. The antidepressant qualities of the dual NET and SERT reuptake inhibitor duloxetine is disclosed in European Patent No. EP 273658. Venlafaxine is disclosed in U.S. Pat. No. 4,535,186 as a reuptake inhibitor of both NE and 5-HT for the treatment of depressive disorders. U.S. Pat. No. 6,635,675 discloses the use of the dual NE and 5-HT reuptake inhibitor milnacipran for the treatment of chronic fatigue syndrome and fibromyalgia syndrome. In addition, dual NE and 5-HT reuptake inhibitors are also disclosed in U.S. Pat. No. 6,136,083 for the treatment of depression. It is also recognized that compounds which inhibit the reuptake of NE, DA, and 5-HT in varying ratios not specifically mentioned here would also be advantageous.

As the first SNRI drug approved, venlafaxine has become one of the first-line choices for depression and anxiety disorder. An active metabolite, desvenlafaxine, is also under clinical development for the treatment of major depressive disorders. Preclinical studies also indicate that desvenlafaxine may be effective in relieving vasomotor symptoms associated with menopause (e.g., hot flashes and night sweats) (Sorbera, et al, *Drugs of Future.*, 31:304 (2006); Albertazzi, *J. Br. Menopause Soc.*, 12:7 (2006)). Desvenlafaxine is reported to be in clinical development for the treatment of fibromyalgia and neuropathic pain, as well as vasomotor symptoms associated with menopause.

In addition to treating major depressive disorder, duloxetine was approved as the first agent for the treatment of painful diabetic neuropathy in the U.S. It also has been used for stress urinary incontinence in women in Europe. In 2007, duloxetine was approved for the treatment of generalized anxiety disorder in the U.S. Most recently, it was approved by the FDA for the management of fibromyalgia.

Milnacipran is currently available for use as an antidepressant in several countries outside the U.S. It is also under clinical development to assess its potential role in the treatment of fibromyalgia syndrome.

After more than a decade of use, bupropion, is considered a safe and effective antidepressant, suitable for use as first-line treatment. In addition, it is approved for smoking cessation and seasonal affective disorder. It is also prescribed off-label to treat the sexual dysfunction induced by SSRIs. Bupropion is often referred to as an atypical antidepressant. It has much lower affinity for the monoamine transporters compared with other monoamine reuptake inhibitors. The mechanism of action of bupropion is still uncertain but may be related to inhibition of dopamine and norepinephrine reuptake transporters as a result of active metabolites. In a recently reported clinical trial, bupropion extended release (XL) had a sexual tolerability profile significantly better than that of escitalopram with similar remission rates and Hospital Anxiety and Depression (HAD) total scores in patients with major depressive disorder (Clayton et al. *J. Clin. Psychiatry*, 67:736 (2006)).

Treating illnesses by inhibiting the reuptake of all three of the monoamines either through combination therapy or "triple inhibitors" may have clinical benefit as well. Triple inhibitors are considered to be the next generation antidepressant (Liang and Richelson, *Primary Psychiatry*, 15(4):50 (2008)). Rationale for inclusion of a dopamine enhancing component in anti-depressant therapy includes observed deficits in dopaminergic function, the success of combination therapy with dopamine agonists and traditional anti-depressants, and an increased sensitivity in dopamine receptors due to chronic anti-depressant administration (Skolnick et al., *Life Sciences*, 73:3175-3179 (2003)). Combination therapy with an SSRI and a noradrenaline and dopamine reuptake inhibitor was shown to be more efficacious in patients with treatment-resistant depression (Lam et al, *J. Clin. Psychiatry*, 65(3):337-340 (2004)). Clinical studies using the combination of bupropion and an SSRI or SNRI have showed improved efficacy for the treatment of MDD in patients refractory to the treatment with SSRIs, SNRIs, or bupropion alone (Zisook et al, *Biol. Psychiat.*, 59:203 (2006); Papkostas, *Depression and Anxiety*, 23:178-181 (2006); Trivedi et al, *New Engl. J. Med.*, 354:1243 (2006)). Other studies using methylphenidate, both immediate release and extended release formula, have shown it to be effective as an augmenting agent in treatment-resistant depression (Patkar et al, *J. Clin. Psychopharmacol.*, 26:653 (2006); Masand et al, *Depression and Anxiety*, 7:89 (1998)). In addition, the combination of bupropion-SR with either SSRIs or norepinephrine and dopamine reuptake inhibitors was found to induce less sexual dysfunction than monotherapy (Kennedy et al, *J. Clin. Psychiatry*, 63(3):181-186 (2002)). As such, inhibitory activity against DA reuptake, in addition to NE and 5-HT reuptake, is expected to provide a more rapid onset of anti-depressant effect than other mixed inhibitors which are selective for NET and SERT over DAT. PCT International Publication Nos. WO 03/101453 and WO 97/30997 disclose a class of compounds which are active against all three monoamine transporters. Also, PCT International Patent Publication No. WO 03/049736 discloses a series of 4-substituted piperidines, each of which displays similar activity against DA, NE, and 5-HT transporters. Bicyclo[2.2.1]heptanes (Axford et al., *Bioorg. Med. Chem. Lett.*, 13:3277-3280 (2003)) and azabicyclo[3.1.0]hexanes (Skolnick et al., *Eur. J. Pharm.*, 461:99-104 (2003)) are also described as triple inhibitors of the three monoamine transporters. 1-(3,4-Dichlorophenyl)-3-azabicyclo[3.1.0]hexane has been shown to be efficacious in treating depression in clinical trials (Beer et al, *J. Clin. Pharmacol.*, 44:1360-1367 (2004)). Current widely used anti-obesity drug sibutramine is believed to work through the inhibition of all three transporters DAT, SERT, and NET (Ryan, *Pharmacotherapy of Obesity*, 245-266 (2004)).

Recent drug approvals with SNRIs for treatment of fibromyalgia and diabetic neuropathy reinforce the utility of this drug class in the treatment of neuropathic pain. Other largely untapped areas which remain to be exploited with this drug class include sexual dysfunction, such as premature ejaculation, irritable bowel syndrome, obesity, neurodegenerative diseases such as Parkinson's disease, restless leg syndrome, and substance abuse and addiction.

There is still a large need for compounds that block the reuptake of norepinephrine, dopamine, and serotonin and treat various neurological and psychological disorders.

The present invention is directed achieving this objective.

SUMMARY OF THE INVENTION

The present invention is directed to a compound of formula (I):

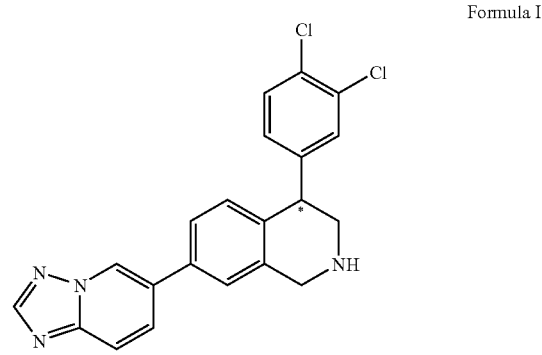 [SMILES: Clc1ccc(C2CNCc3cc(-c4ccc5ncnn5c4)ccc32)cc1Cl]

Formula I wherein:

the carbon atom designated * is in the R or S configuration;

or a pharmaceutically acceptable salt thereof or a solvate thereof.

DETAILED DESCRIPTION OF THE INVENTION

Figure 1:
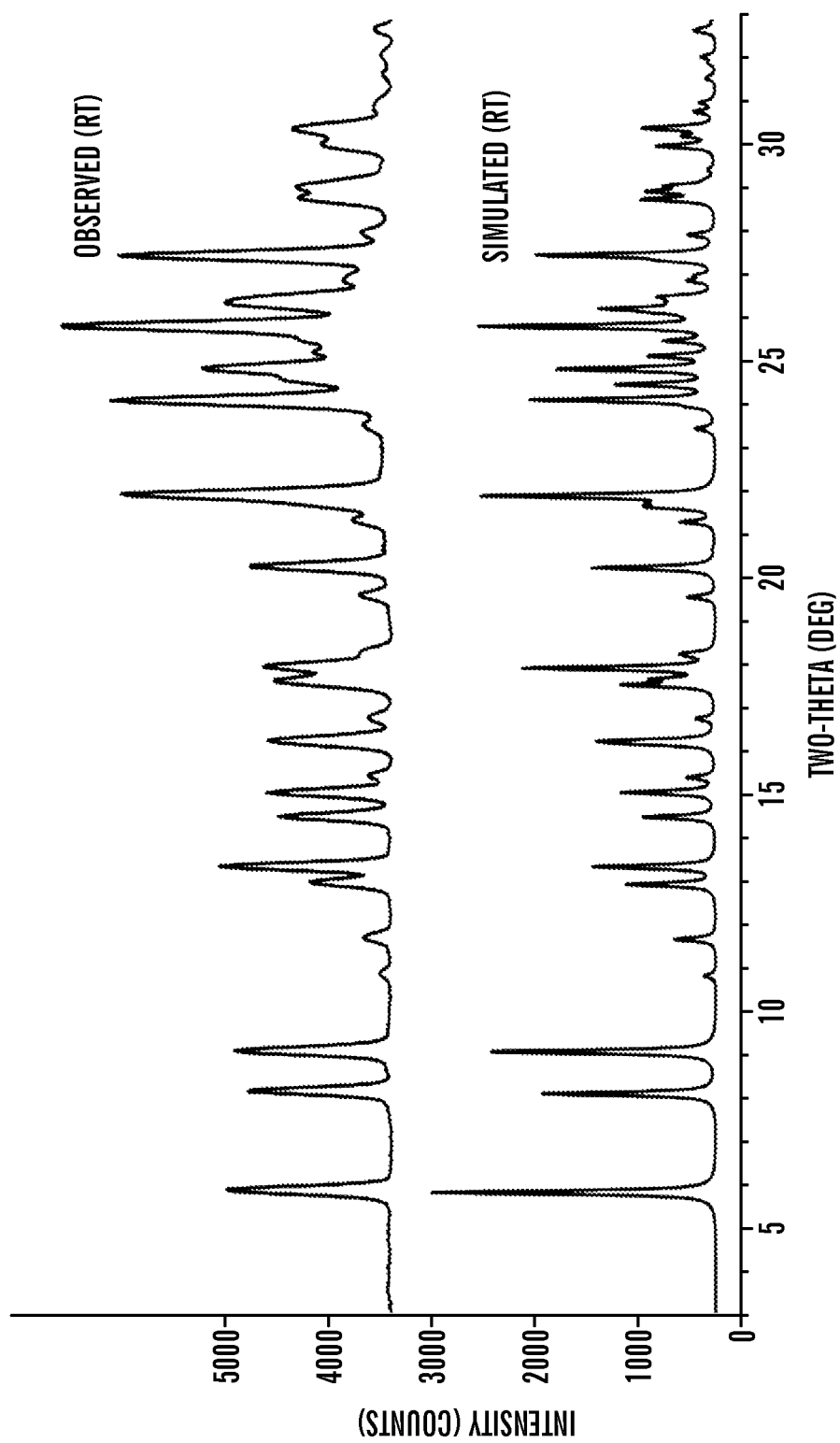
FIG. 1 illustrates experimental and simulated powder X-ray diffraction (PXRD) patterns (CuKα λ=1.54178 Å at T=room temperature) of Form SA-1.

The present invention is directed to a compound of formula (I):

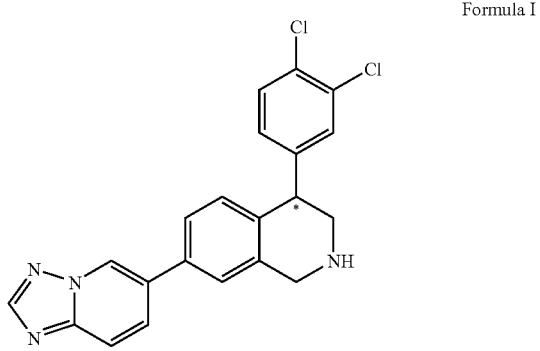 [SMILES: Clc1ccc(C2CNCc3cc(-c4ccc5ncnn5c4)ccc32)cc1Cl]

Formula I wherein:
the carbon atom designated * is in the R or S configuration;
or a pharmaceutically acceptable salt thereof or a solvate thereof.

As used above, and throughout the description of the invention, the following terms, unless otherwise indicated, shall be understood to have the following meanings:

The term "compounds of the invention", and equivalent expressions, are meant to embrace compounds of general formula (I) as hereinbefore described, which expression includes the pharmaceutically acceptable salts and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," *J. Pharm. Sci.*, 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "substantially pure" refers to chemical purity and form purity. For example, substantially pure Form SA-1 (or Form N-2) comprises at least about 95 wt %, preferably at least about 98 wt %, more preferably at least about 99 wt % of Form SA-1 and less than about 5 wt %, preferably less than about 2 wt %, and more preferably less than about 1 wt % of other compounds having a different chemical structure than the S-enantiomer of Formula (I). Additionally, substantially pure Form SA-1 (or Form N-2) comprises at least about 95 wt %, preferably at least about 98 wt %, more preferably at least about 99 wt % of Form SA-1 and less than about 5 wt %, preferably less than about 2 wt %, and more preferably less than about 1 wt % of any other crystalline form of the S-enantiomer of Formula (I). This means that the Form SA-1 (or Form N-2) preferably contains less than about 5 wt % of other compounds, and less than about 5 wt % of any other form (also referred to as "phase homogenicity").

The term "therapeutically effective amounts" is meant to describe an amount of compound of the present invention effective in increasing the levels of serotonin, norepinephrine, or dopamine at the synapse and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

The term "pharmaceutical composition" means a composition comprising a compound of formula (I) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar—agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

In one preferred embodiment of the present invention, the compound of formula (I) is a (+)-stereoisomer.

In another preferred embodiment of the present invention, the compound of formula (I) is a (−)-stereoisomer.

Another more preferred embodiment of the present invention is the compound of formula (I) wherein the carbon atom designated * is in the R configuration.

Another more preferred embodiment of the present invention is the compound of formula (I) wherein the carbon atom designated * is in the S configuration.

In another preferred embodiment of the present invention, the compound of formula (I) is a (S)(+)-stereoisomer.

In yet another preferred embodiment of the present invention, the compound of formula (I) is a (R)(−)-stereoisomer.

Another preferred embodiment of the present invention is a mixture of stereoisomeric compounds of formula (I) wherein * is in the S or R configuration.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula (I), wherein one or more of the atoms, e.g., C or H, are replaced by the corresponding radioactive isotopes of that atom (e.g., C replaced by $^{14}C$ and H replaced by $^{3}H$), or a stable isotope of that atom (e.g., C replaced by $^{13}C$ or H replaced by $^{2}H$). Such compounds have a variety of potential uses, e.g., as standards and reagents in determining the ability of a potential pharmaceutical to bind to neurotransmitter proteins. In addition, in the case of stable isotopes, such compounds may have the potential to favorably modify the biological properties, e.g., pharmacological and/or pharmacokinetic properties, of compounds of formula (I). The details concerning selection of suitable sites for incorporating radioactive isotopes into the compounds are known to those skilled in the art.

Another aspect of the present invention relates to a crystalline form of 7-([1,2,4]triazolo[1,5-a]pyridinyl-6-yl)-4-(3,4-dichlorophenyl)-1,2,3,4-tetrahydroisoquinoline, in particular, Form SA-1 or Form N-2, as described herein. For purposes of clarification, the free base racemate of rac-7-([1,2,4]triazolo[1,5-a]pyridinyl-6-yl)-4-(3,4-dichlorophenyl)-1,2,3,4-tetrahydroisoquinoline is represented by Formula (I). Forms SA-1 and N-2 are particular crystalline forms of the S-enantiomer of Formula (I) ((S)-7-([1,2,4]triazolo[1,5-a]pyridinyl-6-yl)-4-(3,4-dichlorophenyl)-1,2,3,4-tetrahydroisoquinoline), as described herein.

Thus, one embodiment of the present invention relates to Form SA-1. One aspect of this embodiment of the present invention relates to Form SA-1, characterized by the following unit cell parameters:

Cell dimensions:
a=11.0668(9) Å
b=7.3750(6) Å
c=15.3927(14) Å
alpha=90°
beta=100.594(7)°
gamma=90°
Space group: Monoclinic, $P2_1$
Volume: 1234.90(18) Å$^3$
Z, Calculated Density: 2, 1.363 Mg/m$^3$ Another aspect of this embodiment of the present invention relates to Form SA-1, characterized by fractional atomic coordinates within the unit cell as listed in Table 6, Atomic Coordinates.

A further aspect of this embodiment of the present invention relates to Form SA-1 with characteristic peaks in the powder X-ray diffraction pattern at values of 2 theta of 5.8±0.1, 8.1±0.1, 9.1±0.1, 10.8±0.1, 11.7±0.1, 13.0±0.1, 13.3±0.1, 14.5±0.1, 15.1±0.1, 15.4±0.1, 16.2±0.1, and 16.8±0.1, at a temperature between about 20° C. and about 25° C., based on a high quality pattern collected with a diffractometer (cuKα) with a spinning capillary with 2θ calibrated with a National Institute of Standards and Technology (NIST) or other suitable standard.

Another aspect of this embodiment of the present invention relates to Form SA-1 characterized by a melt with decomposition endotherm with onset typically of about 85° C.

A further aspect of this embodiment of the present invention relates to substantially pure Form SA-1.

Another embodiment of the present invention relates to Form N-2. One aspect of this embodiment of the present invention relates to Form N-2, characterized by the following unit cell parameters:

Cell dimensions:
a=7.1183(2) Å
b=21.2160(7) Å
c=26.3602(9) Å
alpha=90°
beta=90°
gamma=90°

Space group: Orthorhombic, $P2_12_12_1$

Volume: 3981.0(2) Å$^3$

Z, Calculated Density: 8, 1.441 Mg/m$^3$

Another aspect of this embodiment of the present invention relates to Form N-2, characterized by fractional atomic coordinates within the unit cell as listed in Table 8, Atomic Coordinates.

A further aspect of this embodiment of the present invention relates to Form N-2 with characteristic peaks in the powder X-ray diffraction pattern at values of 2 theta of 8.3±0.1, 8.9±0.1, 10.9±0.1, 14.2±0.1, 14.7±0.1, 16.7±0.1, 17.3±0.1, 18.0±0.1, 18.4±0.1, 18.8±0.1, 20.2±0.1, and 21.9±0.1, at a temperature between about 20° C. and about 25° C., based on a high quality pattern collected with a diffractometer (cuKα) with a spinning capillary with 2θ calibrated with a NIST or other suitable standard.

Another aspect of this embodiment of the present invention relates to Form N-2 characterized by a melt with decomposition endotherm with onset typically of about 250° C.

A further aspect of this embodiment of the present invention relates to substantially pure Form N-2.

Another aspect of the present invention is a pharmaceutical composition containing a therapeutically effective amount of the compound of formula (I) or a crystalline form as described herein and a pharmaceutically acceptable carrier.

Another aspect of the present invention relates to a method of treating a disorder which is created by or is dependent upon decreased availability of serotonin, norepinephrine, or dopamine. The method involves administering to a patient in need of such treatment a therapeutically effective amount of a compound of formula (I), a crystalline form of a compound of formula (I), or a pharmaceutically acceptable salt thereof. The method of the present invention is capable of treating subjects afflicted with various neurological and psychiatric disorders including, without limitation: attention deficit hyperactivity disorder (ADHD), cognition impairment, anxiety disorders, generalized anxiety disorder (GAD), panic disorder, bipolar disorder or manic depression or manic-depressive disorder, obsessive compulsive disorder (OCD), posttraumatic stress disorder (PTSD), acute stress disorder, social phobia, simple phobias, pre-menstrual dysphoric disorder (PMDD), social anxiety disorder (SAD), major depressive disorder (MDD), postnatal depression, dysthymia, depression associated with Alzheimer's disease, Parkinson's disease, or psychosis, supranuclear palsy, eating disorders, obesity, anorexia nervosa, bulimia nervosa, binge eating disorder, diabetes, ischemic diseases, pain, substance abuse disorders, chemical dependencies, nicotine addiction, cocaine addiction, amphetamine addiction, alcohol addiction, Lesch-Nyhan syndrome, neurodegenerative diseases, Parkinson's disease, late luteal phase syndrome or narcolepsy, psychiatric symptoms, anger, rejection sensitivity, movement disorders, extrapyramidal syndrome, Tic disorders, restless leg syndrome (RLS), tardive dyskinesia, supranuclear palsy, sleep related eating disorder (SRED), night eating syndrome (NES), stress urinary incontinence (SUI), migraine, neuropathic pain, diabetic neuropathy, lower back pain, fibromyalgia syndrome (FS), osteoarthritis pain, arthritis pain, chronic fatigue syndrome (CFS), sexual dysfunction, premature ejaculation, male impotence, thermoregulatory disorders (e.g., hot flashes associated with menopause), and irritable bowel syndrome (IBS).

The compounds/crystalline forms provided herein are particularly useful in the treatment of these and other disorders due, at least in part, to their ability to selectively bind to the transporter proteins for certain neurochemicals with a greater affinity than to the transporter proteins for other neurochemicals.

In another embodiment of the present invention, the above method further involves administering a therapeutically effective amount of a serotonin 1A receptor antagonist or a pharmaceutically acceptable salt thereof. Suitable serotonin 1A receptor antagonists include WAY 100135 and spiperone. WAY 100135 (N-(t-butyl)-3-[a-(2-methoxyphenyl)piperazin-1-yl]-2 phenylpropanamide) is disclosed as having an affinity for the serotonin 1A receptor in U.S. Pat. No. 4,988,814 to Abou-Gharbia et al., which is hereby incorporated by reference in its entirety. Also, Cliffe et al., *J Med Chem* 36:1509-10 (1993), which is hereby incorporated by reference in its entirety, showed that the compound is a serotonin 1A antagonist. Spiperone (8-[4-(4-fluorophenyl)-4-oxobutyl]-1-phenyl-1,3,8-triazaspiro[4,5]decan-4-one) is a well-known compound and is disclosed in U.S. Pat. Nos. 3,155,669 and 3,155,670, which are hereby incorporated by reference in their entirety. The activity of spiperone as a serotonin 1A antagonist is described in Middlemiss et al., *Neurosc and Biobehav Rev.* 16:75-82 (1992), which is hereby incorporated by reference in its entirety.

In another embodiment of the present invention, the above method further involves administering a therapeutically effective amount of a selective neurokinin-1 receptor antagonist or pharmaceutically acceptable salt thereof. Neurokinin-1 receptor antagonists that can be used in combination with the compound of formula (I) or crystalline form, in the present invention are fully described, for example, in U.S. Pat. Nos. 5,373,003, 5,387,595, 5,459,270, 5,494,926, 5,162,339, 5,232,929, 5,242,930, 5,496,833, and 5,637,699; PCT International Patent Publication Nos. WO 90/05525, 90/05729, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; and in U.K. Patent Application Nos. 2 266 529, 2 268 931, 2 269 170, 2 269 590, 2 271 774, 2 292 144, 2 293168, 2 293 169, and 2 302 689; European Patent Publication Nos. EP 0 360 390, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 699 674, 0 707 006, 0 708 101, 0 709 375, 0 709 376, 0 714 891, 0 723 959, 0 733 632 and 0 776 893, which are hereby incorporated by reference in their entirety. The preparations of such compounds are fully described in the aforementioned patents and publications.

In another embodiment of the present invention, the above method further involves administering a therapeutically effective amount of a norepinephrine precursor or a pharmaceutically acceptable salt thereof. Suitable norepinephrine precursors include L-tyrosine and L-phenylalanine.

Another embodiment of the present invention is a method of inhibiting synaptic norepinephrine uptake in a patient in need thereof. The method involves administering a therapeutically effective inhibitory amount of a compound of formula (I) or a crystalline form as described herein.

Another embodiment of the present invention is a method of inhibiting synaptic serotonin uptake in a patient in need thereof. The method involves administering a therapeutically effective inhibitory amount of a compound of formula (I) or a crystalline form as described herein.

Another embodiment of the present invention is a method of inhibiting synaptic dopamine uptake in a patient in need thereof. The method involves administering a therapeutically effective inhibitory amount of a compound of formula (I) or a crystalline form as described herein.

Another embodiment of the present invention is a therapeutic method described herein, where the (+)-stereoisomer of the compound of formula (I) is employed.

Another embodiment of the present invention is a therapeutic method described herein, where the (−)-stereoisomer of the compound of formula (I) is employed.

Another embodiment of the present invention is a kit comprising a compound of formula (I) or a crystalline form as described herein, and at least one compound selected from the group consisting of: a serotonin 1A receptor antagonist compound, a selective neurokinin-1 receptor antagonist compound, and a norepinephrine precursor compound.

Another embodiment of the present invention relates to a method of treating a disorder referred to in the above-mentioned embodiments in a patient in need thereof. The method involves inhibiting synaptic norepinephrine, dopamine, and serotonin uptake by administering a therapeutically effective inhibitory amount of the compound of formula (I) or a crystalline form as described herein, which functions as a triple acting norepinephrine, dopamine, and serotonin uptake inhibitor.

Another embodiment of the present invention relates to a method for inhibiting serotonin uptake in mammals. The method involves administering to a mammal requiring increased neurotransmission of serotonin a pharmaceutically effective amount of the compound of formula (I) or a crystalline form as described herein.

Another embodiment of the present invention relates to a method for inhibiting dopamine uptake in mammals. The method involves administering to a mammal requiring increased neurotransmission of dopamine a pharmaceutically effective amount of the compound of formula (I) or a crystalline form as described herein.

Another embodiment of the present invention relates to a method for inhibiting norepinephrine uptake in mammals. The method involves administering to a mammal requiring increased neurotransmission of norepinephrine a pharmaceutically effective amount of the compound of formula (I) or a crystalline form as described herein.

Another embodiment of the present invention relates to a method of suppressing the desire of humans to smoke. The method involves administering to a human in need of such suppression an effective dose, to relieve the desire to smoke, of the compound of formula (I) or a crystalline form as described herein.

Another embodiment of the present invention relates to a method of suppressing the desire of humans to consume alcohol. The method involves administering to a human in need of such suppression an effective dose, to relieve the desire to consume alcohol, of the compound of formula (I) or a crystalline form as described herein.

Another embodiment of the present invention relates to a process for preparation of a product compound of Formula (I). This process comprises treating a first intermediate compound of Formula (II):

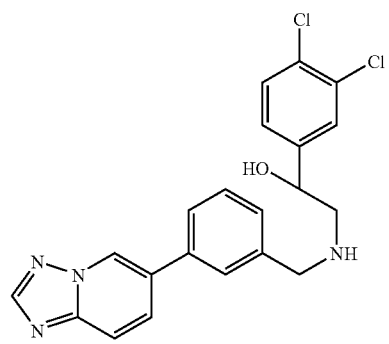

Formula II with an acid under conditions effective to produce the product compound.

Suitable acids include, but are not limited to, sulfuric acid, methansulfonic acid, phosphoric acid, and L-tartaric acid.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates, or products, are prepared as described herein or by the application or adaptation of known methods, by which is meant methods used heretofore or described in the literature.

Compounds useful according to the invention may be prepared by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula (I) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice (e.g., Wuts et al., *Protective Groups in Organic Chemistry* (4$^{th}$ Edition), Wiley (2006), and McOmie, *Protective Groups in Organic Chemistry*, Plenum Press (1973), which are hereby incorporated by reference in their entirety).

The novel tetrahydroisoquinoline reuptake inhibitors of Formula (I) of this invention can be prepared by the synthetic route depicted in Scheme 1.

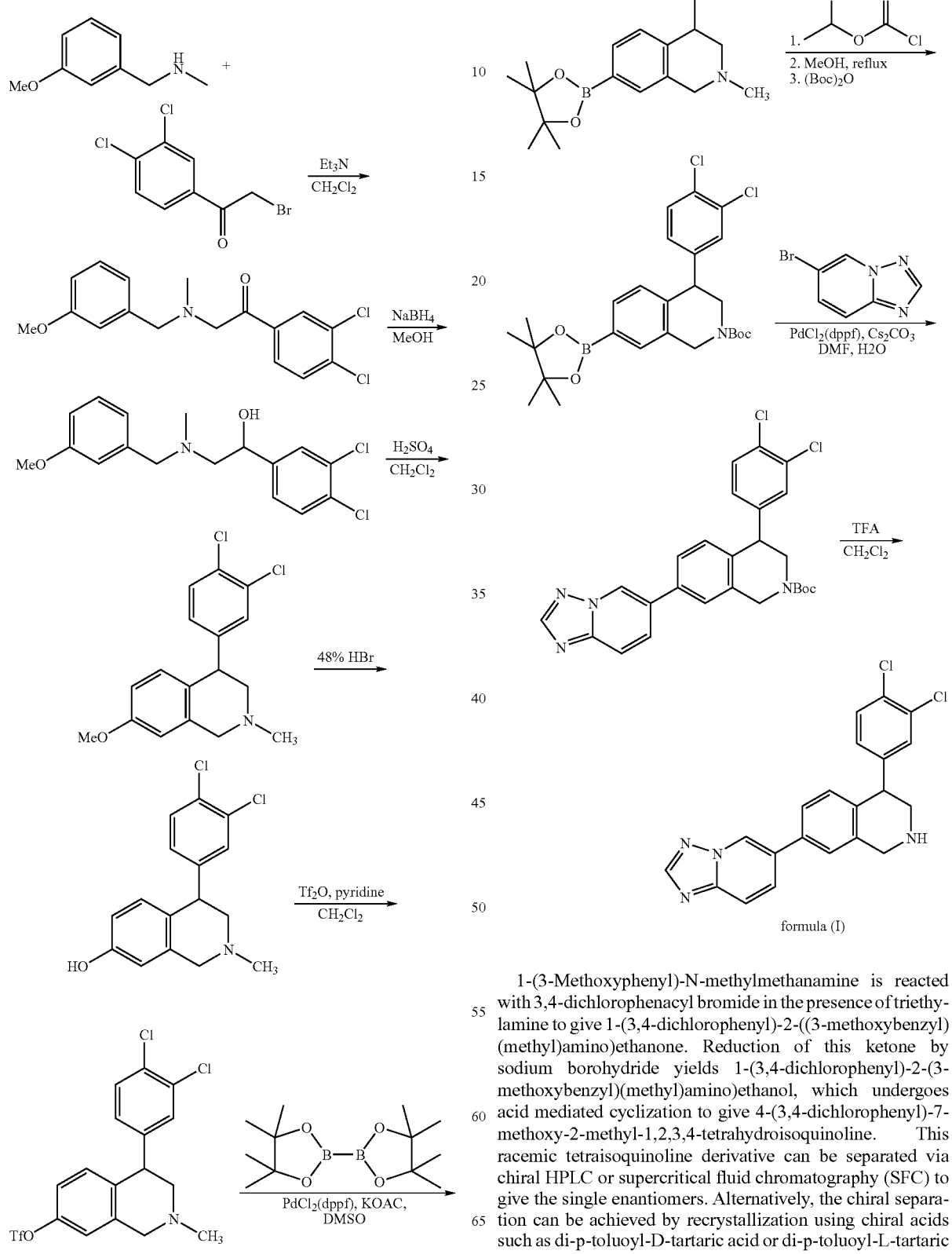

1-(3-Methoxyphenyl)-N-methylmethanamine is reacted with 3,4-dichlorophenacyl bromide in the presence of triethylamine to give 1-(3,4-dichlorophenyl)-2-((3-methoxybenzyl)(methyl)amino)ethanone. Reduction of this ketone by sodium borohydride yields 1-(3,4-dichlorophenyl)-2-(3-methoxybenzyl)(methyl)amino)ethanol, which undergoes acid mediated cyclization to give 4-(3,4-dichlorophenyl)-7-methoxy-2-methyl-1,2,3,4-tetrahydroisoquinoline. This racemic tetraisoquinoline derivative can be separated via chiral HPLC or supercritical fluid chromatography (SFC) to give the single enantiomers. Alternatively, the chiral separation can be achieved by recrystallization using chiral acids such as di-p-toluoyl-D-tartaric acid or di-p-toluoyl-L-tartaric acid.

The 4-(3,4-dichlorophenyl)-7-methoxy-2-methyl-1,2,3,4-tetrahydroisoquinoline is converted to the correspondent phenol by the treatment with 48% HBr under reflux. The resulting phenol is then converted the correspondent triflate which is further transformed to the correspondent pinacol borate derivative 4-(3,4-dichlorophenyl)-2-methyl-7-(4,4,5,5-tetramethyl-1,3,2-dioxaborolan-2-yl)-1,2,3,4-tetrahydroisoquinoline. Demethylation using 1-chloroethyl chloroformate followed by Boc protection gives tert-butyl 4-(3,4-dichlorophenyl)-7-(4,4,5,5-tetramethyl-1,3,2-dioxaborolan-2-yl)-3,4-dihydroisoquinoline-2(1H)-carboxylate. Reaction of this Boc protected tetraisoquinoline with 6-bromo-[1,2,4]triazolo[1,5-a]pyridine under Suzuki coupling conditions affords tert-butyl 7-([1,2,4]triazolo[1,5-a]pyridin-6-yl)-4-(3,4-dichlorophenyl)-3,4-dihydroisoquinoline-2(1H)-carboxylate, which is then deprotected by TFA to give 7-([1,2,4]triazolo[1,5-a]pyridin-6-yl)-4-(3,4-dichlorophenyl)-1,2,3,4-tetrahydroisoquinoline or formula (I).

An alternative synthetic route of preparing compounds of Formula (I) in this invention is depicted in Scheme 2.

Suzuki coupling of 3-formylphenylboronic acid and 6-bromo-[1,2,4]triazolo[1,5-a]pyridine gives 3-([1,2,4]triazolo[1,5-a]pyridin-6-yl)benzaldehyde. This aldehyde undergoes a reductive amination to give 2-(3-([1,2,4]triazolo[1,5-a]pyridin-6-yl)benzylamino)-1-(3,4-dichlorophenyl)ethanol, which is then subjected to sulfuric acid mediated cyclization to provide 7-([1,2,4]triazolo[1,5-a]pyridin-6-yl)-4-(3,4-dichlorophenyl)-1,2,3,4-tetrahydroisoquinoline.

A synthetic route of preparing L-tartrate salts of the present invention is depicted in Scheme 3.

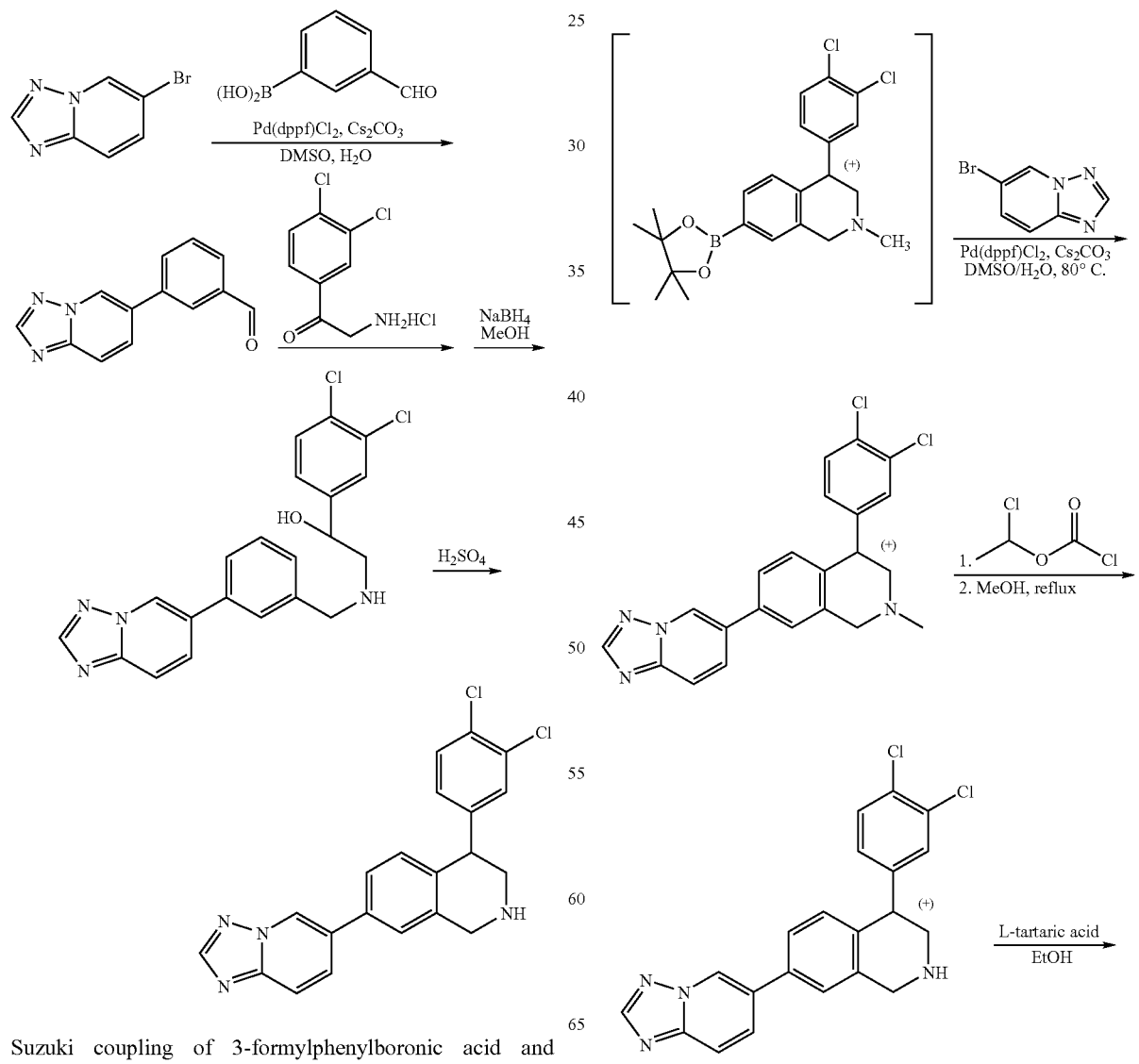

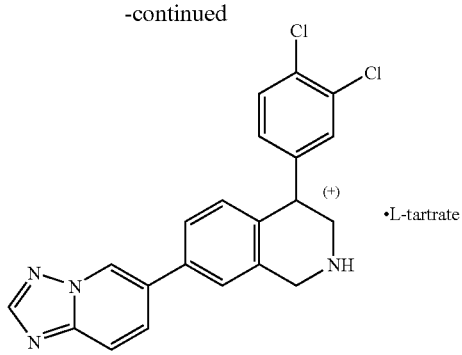

Compounds of formula (I) may be obtained in enantiomerically enriched (R) and (S) form by crystallization with chiral salts as well known to one skilled in the art, or alternatively, may be isolated through chiral HPLC employing commercially available chiral columns.

It will be appreciated that compounds according to the present invention may contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallization techniques, or they are separately prepared from the appropriate isomers of their intermediates.

Radiolabelled compounds of the invention are synthesized by a number of techniques well known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents for identifying areas of the brain or central nervous system that may be affected by disorders where norepinephrine, dopamine, or serotonin transporters and their uptake mechanism are implicated.

Crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs. Crystals of drugs, including polymorphs, methods of preparation, and characterization of drug crystals are discussed in Bryn et al., *Solid-State Chemistry of Drugs*, $2^{nd}$ Edition, SSCI, West Lafayette, Ind. (1999), which is hereby incorporated by reference in its entirety.

For crystallization techniques that employ solvent, the choice of solvent or solvents is typically dependent upon one or more factors, such as solubility of the compound, crystallization technique, and vapor pressure of the solvent, or the ability to afford a substantially pure crystalline form. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility.

In one method to prepare crystals, a compound is suspended and/or stirred in a suitable solvent to afford a slurry, which may be heated to promote complete or partial dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product and/or afford a substantially pure crystalline form. Accordingly, calculation of the amount of seeds needed depends on the size of the seed available and the desired size of an average product particle as described, for example, in Mullin et al., "Programmed Cooling of Batch Crystallizers," *Chemical Engineering Science*, 26:369-377 (1971), which is hereby incorporated by reference in its entirety. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity of the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, X-Ray powder diffraction, or the like, to assure formation of the preferred crystalline form of the product. The resulting crystalline form is typically produced in an amount of greater than about 70 weight percent isolated yield, preferably greater than 90 weight percent isolated yield, based on the weight of the compound originally employed in the crystallization procedure. The product may be co-milled or passed through a mesh screen to delump the product, if necessary.

Crystalline forms may be prepared, for example, directly from the reaction medium of the process for preparing a compound of formula (I). This may be achieved, for example, by employing in the final process step a solvent or a mixture of solvents from which Form SA-1 or Form N-2 may be crystallized. Alternatively, crystalline forms may be obtained by distillation or solvent addition techniques. Suitable solvents for this purpose include, for example, non-polar solvents and polar solvents, including protic polar solvents such as alcohols, and aprotic polar solvents such as ketones, the details and selection of which are known to those skilled in the art.

The presence of more than one polymorph in a sample may be determined by techniques such as powder X-Ray diffraction (PXRD) or solid state nuclear magnetic resonance spectroscopy (SSNMR). For example, the presence of extra peaks in an experimentally measured PXRD pattern when compared with a simulated PXRD pattern may indicate more than one polymorph in the sample. The simulated PXRD may be calculated from single crystal X-Ray data (see Smith, "*A FORTRAN Program for Calculating X-Ray Powder Diffraction Patterns*," Lawrence Radiation Laboratory, Livermore, Calif., UCRL-7196 (April 1963), which is hereby incorporated by reference in its entirety). In one aspect, Form SA-1 or Form N-2 has phase homogeneity indicated by less than 5 percent, preferably less than 2 percent, and more preferably less than 1 percent of the total peak area in the experimentally measured PXRD pattern arising from the extra peaks that are absent from a simulated PXRD pattern.

Preferably, the crystallization technique provides a product comprising substantially pure Form SA-1 or Form N-2. The crystallized material preferably comprises at least 95 wt % of Form SA-1/Form N-1, based on the weight of the compound of formula (I) in the composition. The remaining material may comprise other form(s) of the compound and/or reaction impurities and/or processing impurities arising from its preparation. The presence of reaction impurities and/or processing impurities may be determined by analytical techniques known in the art, such as, for example, chromatography, nuclear magnetic resonance spectroscopy, mass spectrometry, or infrared spectroscopy.

Form SA-1 and Form N-1 can be characterized using various techniques, which are well known to those of ordinary skill in the art. Examples of characterization methods include, but are not limited to, single crystal X-Ray diffraction, powder X-Ray diffraction (PXRD), simulated powder X-Ray patterns (Yin et al., *American Pharmaceutical Review*, 6(2):80 (2003), which is hereby incorporated by reference in its entirety), differential scanning calorimetry (DSC), solid-state $^{13}$C NMR (Earl et al., *J. Magn. Reson.*, 48:35-54 (1982), which is hereby incorporated by reference in its entirety), Raman spectroscopy, infrared spectroscopy, moisture sorption isotherms, thermogravimetric analysis (TGA), and hot stage techniques.

The forms may be characterized and distinguished using single crystal X-ray diffraction, which is based on unit cell measurements of a single crystal of Form SA-1 or Form N-2. A detailed description of unit cells is provided in Stout et al., X-Ray Structure Determination: A Practical Guide, Macmillan Co., New York (1968), Chapter 3, which is hereby incorporated by reference in its entirety. Alternatively, the unique arrangement of atoms in spatial relation within the crystalline lattice may be characterized according to the observed fractional atomic coordinates. Another means of characterizing the crystalline structure is by powder X-ray diffraction analysis in which the diffraction profile is compared to a simulated profile representing pure powder material, both run at the same analytical temperature, and measurements for the subject form characterized as a series of 2θ values.

One of ordinary skill in the art will appreciate that an X-ray diffraction pattern may be obtained with a measurement of error that is dependent upon the measurement conditions employed. In particular, it is generally known that intensities in an X-ray diffraction pattern may fluctuate depending upon measurement conditions employed. It should be further understood that relative intensities may also vary depending upon experimental conditions, and, accordingly, the exact order of intensity should not be taken into account. Additionally, a measurement error of diffraction angle for a conventional X-ray diffraction pattern is typically about 5 percent or less, and such degree of measurement error should be taken into account as pertaining to the aforementioned diffraction angles. Consequently, it is to be understood that the crystal forms of the present disclosure are not limited to the crystal forms that provide X-ray diffraction patterns completely identical to the X-ray diffraction patterns depicted in the accompanying Figures disclosed herein. Any crystal form that provides an X-ray diffraction pattern, and DSC thermogram substantially identical to those disclosed in the accompanying Figures fall within the scope of the present disclosure. The ability to ascertain substantial identities of X-ray diffraction patterns is within the purview of one of ordinary skill in the art.

The present invention provides compositions containing the compounds/crystalline forms described herein, including, in particular, pharmaceutical compositions comprising therapeutically effective amounts of the compounds/crystalline forms and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formula (I) or a crystalline form as described herein and the additional active ingredient (alone or in combination with diluent or carrier) selected from a serotonin 1A receptor antagonist, a selective neurokinin-1 receptor antagonist, and a norepinephrine precursor.

In practice, the compounds/crystalline forms of the present invention may generally be administered parenterally, intravenously, subcutaneously, intramuscularly, colonically, nasally, intraperitoneally, rectally, or orally.

The products according to the present invention may be presented in forms permitting administration by the most suitable route and the invention also relates to pharmaceutical compositions containing at least one product according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate, and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

For parenteral administration, emulsions, suspensions, or solutions of the products according to the invention in vegetable oil, for example sesame oil, groundnut oil, or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride, and that they are sterilized by heating, irradiation, or microfiltration.

Suitable compositions containing the compounds/crystalline forms of the present invention may be prepared by conventional means. For example, compounds/crystalline forms of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I)/crystalline form.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

The present invention provides compounds which inhibit synaptic norepinephrine, dopamine, and serotonin uptake and are, therefore, believed to be useful in treating a disorder which is created by or is dependent upon decreased availability of serotonin, norepinephrine, or dopamine. Although the compounds of formula (I) inhibit synaptic norepinephrine, dopamine, and serotonin uptake, in any individual compound, these inhibitory effects may be manifested at the same or vastly different concentrations or doses. As a result, the compounds of formula (I) are useful in treating such a disorder at doses at which synaptic norepinephrine uptake may be substantially inhibited but at which synaptic serotonin uptake or dopamine uptake is not substantially inhibited, or vice versa. Also, the compounds of formula (I) are useful in treating such a disorder at doses at which synaptic dopamine uptake may be substantially inhibited but at which synaptic norepinephrine or serotonin uptake is not substantially inhibited, or vice versa. And, conversely, the compounds of formula (I) are useful in treating such a disorder at doses at which synaptic serotonin uptake may be substantially inhibited but at which synaptic norepinephrine or dopamine uptake is not substantially inhibited, or vice versa. The compounds of formula (I) may also be useful in treating such a disorder at doses at which synaptic norepinephrine, dopamine, and serotonin uptake are substantially inhibited.

The concentrations or doses at which a test compound inhibits synaptic norepinephrine, dopamine, and serotonin uptake is readily determined by the use of standard assay and techniques well known and appreciated by one of ordinary skill in the art. For example, the degree of inhibition at a particular dose in rats can be determined by the method of Dudley, *J Pharmacol Exp Ther*, 217:834-840 (1981), which is hereby incorporated by reference in its entirety.

The therapeutically effective inhibitory dose is one that is effective in substantially inhibiting synaptic norepinephrine uptake, synaptic dopamine uptake, or synaptic serotonin uptake or inhibiting the synaptic uptake of two or more of norepinephrine, dopamine, and serotonin uptake. The therapeutically effective inhibitory dose can be readily determined by those skilled in the art by using conventional range finding techniques and analogous results obtained in the test systems described above.

Compounds of this invention provide a particularly beneficial therapeutic index relative to other compounds available for the treatment of similar disorders. Without intending to be limited by theory, it is believed that this is due, at least in part, to the compounds having higher binding affinities for one or two of the neurotransmitter transporters, e.g., selectivity towards the serotonin transporter protein ("SERT") over the transporters for other neurochemicals, e.g., the dopamine transporter protein ("DAT") and the norepinephrine transporter protein ("NET").

Binding affinities are demonstrated by a number of means well known to ordinarily skilled artisans, including, without limitation, those described in the Examples section below. Briefly, for example, protein-containing extracts from cells, e.g., HEK293E cells, expressing the transporter proteins are incubated with radiolabelled ligands for the proteins. The binding of the radioligands to the proteins is reversible in the presence of other protein ligands, e.g., the compounds of the present invention; said reversibility, as described below, provides a means of measuring the compounds' binding affinities for the proteins ($IC_{50}$ or Ki). A higher $IC_{50}$/Ki value for a compound is indicative that the compound has less binding affinity for a protein than is so for a compound with a lower $IC_{50}$/Ki; conversely, lower $IC_{50}$/Ki values are indicative of greater binding affinities.

Accordingly, the difference in compound selectivity for proteins is indicated by a lower $IC_{50}$/Ki for the protein for which the compound is more selective, and a higher $IC_{50}$/Ki for the protein for which the compound is less selective. Thus, the higher the ratio in $IC_{50}/Ki$ values of a compound for protein A over protein B, the greater is the compounds' selectivity for the latter over the former (the former having a higher $IC_{50}/Ki$ and the latter a lower $IC_{50}/Ki$ for that compound).

The compounds ("triple action transporter reuptake inhibitors") of the present invention have potent binding affinity simultaneously for all three of the biogenic amine transporters, NET, DAT, or SERT. For example, the compounds of this invention possess potent NET, DAT, & SERT $IC_{50}/Ki$ values of less than 200 nM.

The in vivo affinity of the compounds to the three transporter proteins, SERT, DAT, and NET are demonstrated by means well known to those of ordinary skill in the art, including, without limitation, those described in the Examples section below.

Accordingly, the difference in compound selectivity in vivo for protein is indicated by a higher percent occupancy value (or percent inhibition of the [$^3$H] ligand compound used in the Examples section) at the transporter protein for which the compound is more selective, and a lower percent occupancy (or percent inhibition of the $^3$[H] ligand compound used in the Examples section) for the protein for which the compound is less selective.

The compounds of the present invention, when administrated at a pharmaceutically feasible dose via means such as, but not limited to, oral, intravenous, subcutaneous, intraperitoneal and intramuscular, have statistically significant percent occupancy value(s) at one, two or all of the biogenic amine transporters NET, DAT, or SERT.

The compounds of the present invention, when administrated at a pharmaceutically feasible dose via means such as, but not limited to, oral, intravenous, subcutaneous, intraperitoneal and intramuscular, have 10%-100% occupancy value(s) at one, two or all of the biogenic amine transporters NET, DAT, or SERT. In a preferred embodiment, compounds of the present invention have 40%-100% occupancy value(s) at at least one the biogenic amine transporters NET, DAT, or SERT.

EXAMPLES

Example 1

Preparation of 7-([1,2,4]triazolo[1,5-a]pyridin-6-yl)-4-(3,4-dichlorophenyl)-1,2,3,4-tetrahydroisoquinoline, L-Tartrate Salt Step A: To a solution of 3-methoxybenzaldehyde (180 g, 1.32 mol) in methanol (1 L) was added a 40% aqueous solution of methylamine (113 ml, 1.31 mol) followed by 1 hour stirring at 0° C. Sodium borohydride (75 g, 1.98 mol) was added portionwise at 0° C. and the reaction mixture was stirred for 1 hour. The solution was concentrated to a smaller volume then, was diluted with water (200 mL) and the resulting solution was extracted with methylene chloride (3×500 mL). The combined organic extracts were dried over sodium sulfate, filtered, and concentrated under reduced pressure to afford the crude N-methylbenzylamine (220 g, quantitative) as clear oil, which was used in the next step without further purification: $^1$H NMR (CDCl$_3$, 500 MHz) δ.7.23 (t, J=8.0 Hz, 1H), 6.92-6.88 (m, 2H), 6.81-6.78 (m, 1H), 3.80 (s, 3H), 3.73 (s, 2H), 2.45 (s, 3H), 2.07 (broad s, 1H).

Step B: To a solution of the above amine (6.2 g, 41.00 mmol) from Step A in methylene chloride (100 mL) was added 3,4-dichlorophenacyl bromide (10.0 g, 37.3 mmol) and the resulting mixture was stirred at 0° C. for 1 hour prior to the addition of triethylamine (5.20 mL, 37.31 mmol), followed by 1 hour stirring at 0° C. The reaction mixture was diluted with water (100 mL) then the aqueous phase was extracted with additional methylene chloride (3×75 mL). The combined extracts were dried over sodium sulfate, filtered, and concentrated to afford 1-(3,4-dichlorophenyl)-2-(3-methoxybenzyl)(methyl)amino)ethanone (15.08 g) as a light yellow oil, which was used in the next step without further purification: $^1$H NMR (500 MHz, CDCl$_3$) δ 8.08 (d, J=2.0 Hz, 1H), 7.78 (dd, J=8.5; 2.0 Hz, 1H), 7.50 (d, J=8.5 Hz, 1H), 7.25 (d, J=8.5 Hz, 1H), 6.90 (d, J=7.5 Hz, 1H), 6.87 (d, J=2.5 Hz, 1H), 6.82 (dd, J=8.0; 2.5 Hz, 1H), 3.79 (s, 3H), 3.66 (s, 2H), 3.60 (s, 2H), 2.33 (s, 3H).

Step C: To a solution of the ketone (~37 mmol) from Step B in methanol (150 mL), was added sodium borohydride (2.11 g, 55.79 mmol) portionwise at 0° C. The reaction mixture was first stirred for 2 hours then, was diluted with water (100 mL) and extracted with methylene chloride (3×300 mL). The combined organic extracts were dried over sodium sulfate, filtered, and concentrated to dryness under reduced pressure to afford the crude alcohol (14.14 g) as a yellow oil, which was used without further purification in the next step: $^1$H NMR (500 MHz, CDCl$_3$) δ 7.45 (d, J=2.0 Hz, 1H), 7.38 (d, J=8.0 Hz, 1H), 7.28-7.23 (m, 1H), 7.16 (dd, J=8.0; 2.0 Hz, 1H), 6.90-6.81 (m, 3H), 4.70-4.65 (m, 1H), 3.81 (s, 3H), 3.70 (d, J=13.0 Hz, 1H), 3.50 (d, J=13.0 Hz, 1H), 2.54-2.49 (m, 2H), 2.32 (s, 3H).

Step D: To a solution of the alcohol (~37 mmol) from Step C in methylene chloride (200 mL) was added concentrated sulfuric acid (12 mL, 235 mol) and the mixture was stirred at 0° C. for 28 hours. The reaction was quenched by adding a 6N NaOH solution till pH~9. The aqueous phase was extracted with additional methylene chloride (3×). The combined organic extracts were washed with brine (3×), dried over sodium sulfate, filtered, and concentrated. The residue was purified by flash chromatography (1:1:1: to 1:1:2 dichloromethane/hexanes/ethyl acetate) to afford 4-(3,4-dichlorophenyl)-7-methoxy-2-methyl-1,2,3,4-tetrahydroisoquinoline (7.0 g, 59% over 3 steps) as a light yellow oil: $^1$H NMR (500 MHz, CDCl$_3$) δ 7.33 (d, J=8.0 Hz, 1H), 7.29 (d, J=2.0 Hz, 1H), 7.03 (dd, J=8.5; 2.0 Hz, 1H), 6.76 (d, J=8.5 Hz, 1H), 6.66 (dd, J=8.5; 3.0 hz, 1H), 6.61 (d, J=2.5 Hz, 1H), 4.16-4.11 (m, 1H), 3.77 (s, 3H), 3.67-3.59 (m, 2H), 2.92 (dd, J=11.5; 5.5 Hz, 1H), 2.55 (dd, J=11.5; 7.0 Hz, 1H), 2.39 (s, 3H). The undesired 5-methoxy isomer was also isolated (1.20 g, 10% over 3 steps).

Step E: The racemic 4-(3,4-dichlorophenyl)-7-methoxy-2-methyl-1,2,3,4-tetrahydroisoquinoline (7.0 g) from Step D above was resolved by preparative chiral HPLC (CHIRAL-PAK AD column, using 80:20:0.1 heptane/2-propanol/diethylamine as the eluent) to give the (+)-enantiomer ($[\alpha]^{25}_D$+ 31.9° (c 0.49, methanol)) (3.68 g) as a colorless oil and the (−)-enantiomer (3.99 g) as a colorless oil.

Step F: A solution of (+)-4-(3,4-dichlorophenyl)-7-methoxy-2-methyl-1,2,3,4-tetrahydroisoquinoline (3.68 g, 11.42 mmol) in a mixture of acetic acid (20 mL) and 48% aqueous hydrobromic acid solution (50 mL) was refluxed for 8 hours. The ice-cold reaction mixture was basified with a concentrated aqueous solution of sodium hydroxide and a saturated aqueous solution of sodium bicarbonate until reaching a pH of about 8-9 and was extracted with dichloromethane (3×). The combined extracts were dried over sodium sulfate, filtered, and concentrated in vacuo to afford the crude alcohol (2.6 g) as a yellow solid. $^1$H NMR (500 MHz, CDCl$_3$) δ 7.32 (d, J=8.5 Hz, 1H), 7.26 (d, J=2.0 Hz, 1H), 7.01 (dd, J=8.0; 2.0 Hz, 1H), 6.65 (d, J=8.0 Hz, 1H), 6.54 (d, J=8.5 Hz, 1H), 6.49 (broad s, 1H), 4.15-4.10 (m, 1H), 3.60 (d, J=15.0 Hz, 1H), 3.56 (d, J=15.0 Hz, 1H), 2.96 (dd, J=11.5; 5.7 Hz, 1H), 2.52 (dd, J=11.5, 8.0 Hz, 1H), 2.39 (s, 3H).

Step G: To a solution of the phenol from Step F above (2.1 g, 6.81 mmol) and pyridine (0.72 mL, 8.85 mmol) in dichloromethane (60 mL) was added trifluoromethanesulfonic anhydride (1.37 mL, 8.14 mmol) at −78° C. The reaction was allowed to warm to 0° C. and stirred for 1 hour. The reaction mixture was diluted with water (20 mL) and extracted with dichloromethane (3×). The combined extracts were dried over sodium sulfate, filtered, and concentrated to give the crude triflate as a yellow oil. $^1$H NMR (500 MHz, CDCl$_3$) δ 7.36 (d, J=8.5 Hz, 1H), 7.30 (d, J=2.0 Hz, 1H), 7.03-6.98 (m, 3H), 6.94 (d, J=8.5 Hz, 1H), 4.19-4.15 (m, 1H), 3.68 (s, 2H), 2.96 (dd, J=11.7; 5.5 Hz, 1H), 2.60 (dd, J=11.7, 7.5 Hz, 1H), 2.42 (s, 3H).

Step H: A mixture of the triflate from Step G above (~6.8 mmol), bis(pinacolato)diboron (2.07 g, 8.15 mmol), and potassium acetate (2.05 g, 20.8 mmol) in dimethyl sulfoxide (35 mL) was degassed with argon. To this mixture was added dichloro[1,1'-bis(diphenylphosphino)ferrocene]palladium (II) (0.40 g, 0.55 mmol). The resulting mixture was degassed with argon and then heated at 85° C. for 2 hours. The cold reaction mixture was diluted with ethyl acetate (150 mL). The resulting solution was washed with water (2×40 mL), brine (1×40 mL), dried over sodium sulfate, filtered, and concentrated in vacuo. A Purification flash chromatography column (eluent, 1:1:1 to 1:1:2 dichloromethane/hexanes/ethyl acetate) gave the desired boronate ester (2.6 g, 91% over 2 steps) as a yellow solid. $^1$H NMR (500 MHz, CDCl$_3$) δ 7.55 (s, 1H), 7.52 (d, J=7.5 Hz, 1H), 7.33 (d, J=8.5 Hz, 1H), 7.28 (d, J=2.0 Hz, 1H), 7.01 (dd, J=8.0, 2.0 Hz, 1H), 6.85 (d, J=8.0 Hz, 1H), 4.23 (t, J=6.5 Hz, 1H), 3.71 (d, J=15.0 Hz, 1H), 3.67 (d, J=15.0 Hz, 1H), 2.98 (dd, J=11.4, 5.3 Hz, 1H), 2.56 (dd, J=11.4, 7.5 Hz, 1H), 2.41 (s, 3H), 1.33 (s, 12H).

Step I: To a solution of the boronate ester (2.6 g, 6.22 mmol) from Step F and proton sponge (2.6 g, 12.1 mmol) in dichloroethane (80 mL) at 0° C. was added 1-chloroethyl chloroformate (2.4 mL, 22.1 mmol). The mixture was stirred at 0° C. for 15 minutes, then was refluxed for 40 minutes and was concentrated in vacuo. The residue was filtered through a short pad of silica gel (eluent, 1:1:1 dichloromethane/hexanes/ethyl acetate) and the filtrate was concentrated in vacuo. The residue was diluted with methanol (160 mL), heated to reflux for 1 hour and concentrated in vacuo to give the 4-(3,4-dichlorophenyl)-7-(4,4,5,5-tetramethyl-1,3,2-dioxaborolan-2-yl)-1,2,3,4-tetrahydroisoquinoline as a brown foam.

Step J: A solution of the product from Step I (~6.2 mmol), (Boc)$_2$O (3.60 g, 16.4 mmol), triethylamine (1.5 mL, 10.7 mmol) and DMAP (0.26 g, 2.20 mmol) in dichloromethane (120 mL) was stirred at room temperature for 4 hours. The reaction was quenched by the addition of water (50 mL) then, the aqueous phase was extracted with additional dichloromethane (2×100 mL). The combined extracts were dried over sodium sulfate, filtered, and concentrated in vacuo. A purification by flash column chromatography (eluent, 47.5: 47.5:5 to 1:1:1 dichloromethane/hexanes/ethyl acetate) gave the boc-protected tetrahydroisoquinoline (1.82 g, 58% over 3 steps) as a white foam. $^1$H NMR (500 MHz, CDCl$_3$) δ 7.65 (s, 1H), 7.58 (d, J=7.5 Hz, 1H), 7.32 (d, J=8.0 Hz, 1H), 7.13 (s, 1H), 6.95 (d, J=7.0 Hz, 1H), 6.97-6.93 and 6.83-6.78 (m, 1H), 5.01-4.95 and 4.48-4.43 (m, 1H), 4.56-4.52 (m, 1H), 3.95 (s, 1H), 3.83-3.44 (m, 2H), 1.43 and 1.26 (2s, 9H), 1.33 (s, 12H).

Step K: A dry flask was loaded with the boronate ester (0.8 g, 1.59 mmol) from Step J, 6-bromo-[1,2,4]triazolo[1,5-a]pyridine (0.35 g, 1.78 mmol), cesium carbonate (0.97 g, 2.98 mmol), and dichloro[1,1'-bis(diphenylphosphino)ferrocene]palladium(II) dichloromethane adduct (87 mg, 0.12 mmol). The flask was blanketed with argon then, DMF (20 mL) and water (4 mL) were added followed by a short sonication. The reaction mixture was heated to 80° C. for 1 hour. The cold reaction mixture was diluted with water (20 mL) and the aqueous layer was extracted with dichloromethane (3×60 mL). The combined organic phases were concentrated in vacuo. Purification by flash column chromatography (eluent, 1:1:1 to 1:1:2 dichloromethane/hexanes/ethyl acetate) gave the Boc-protected 7-([1,2,4]triazolo[1,5-a]pyridin-6-yl)-4-(3,4-dichlorophenyl)-1,2,3,4-tetrahydroisoquinoline (0.86 g, quantitative) as a white foam.

Step L: A solution of the Boc-protected 7-([1,2,4]triazolo[1,5-a]pyridin-6-yl)-4-(3,4-dichlorophenyl)-1,2,3,4-tetrahydroisoquinoline (0.85 g, 1.72 mmol) and concentrated hydrochloric acid (4.0 mL) in ethanol (10 mL) was stirred at room temperature for 1 hour. The reaction mixture was concentrated to dryness in vacuo. The residue was dissolved in a mixture of dichloromethane (14 mL) and TFA (10 mL), stirred at room temperature for 1 hour then concentrated in vacuo. The syrup thus obtained was diluted with dichloromethane and treated with a saturated aqueous solution of sodium bicarbonate until pH 8-9. The aqueous phase was extracted with additional dichloromethane (3×) and the organic phases were dried over sodium sulfate, filtered, and concentrated in vacuo to give 7-([1,2,4]triazolo[1,5-a]pyridin-6-yl)-4-(3,4-dichlorophenyl)-1,2,3,4-tetrahydroisoquinoline (0.59 g, 87%) as a white foam.

Step M: To a solution of the product (0.59 g, 1.49 mmol) from Step B in ethanol was added L-tartaric acid (0.22 g, 1.49 mmol). The slurry was filtered. The cake was rinsed with ethanol and dried to give 7-([1,2,4]triazolo[1,5-a]pyridin-6-yl)-4-(3,4-dichlorophenyl)-1,2,3,4-tetrahydroisoquinoline, L-tartrate salt (0.49 g, 59%, AUC HPLC >99%) as a white solid. $[[\alpha]^{25}_D$+9.0° (c 0.11, methanol)]. $^1$H NMR (500 MHz, CD$_3$OD) δ 9.09 (s, 1H), 8.53 (s, 1H), 8.02 (dd, J=9.0, 2.0 Hz, 1H), 7.86 (d, J=9.0 Hz, 1H), 7.68 (s, 1H), 7.64-7.61 (m, 1H), 7.55 (d, J=8.0 Hz, 1H), 7.48 (d, J=2.0 Hz, 1H), 7.24 (dd, J=8.0, 2.0 Hz, 1H), 7.04 (d, J=8.0 Hz, 1H), 4.65-4.57 (m, 2H), 4.52 (d, J=16.0 Hz, 1H), 4.41 (s, 2H), 3.79 (dd, J=12.5, 6.0 Hz, 1H), 3.44 (t, J=12.5 Hz, 1H). ESI MS m/z 395 [M+H]$^+$. Anal. Calcd. for C$_{21}$H$_{16}$Cl$_2$N$_4$.C$_4$H$_6$O$_6$.0.5H$_2$O: C, 54.16; H, 4.18; N, 10.11. Found: C, 54.07; H, 3.92; N, 9.97.

The L-tartrate of the (−)-7-([1,2,4]triazolo[1,5-a]pyridin-6-yl)-4-(3,4-dichlorophenyl)-1,2,3,4-tetrahydroisoquinoline was prepared using (−)-4-(3,4-dichlorophenyl)-7-methoxy-2-methyl-1,2,3,4-tetrahydroisoquinoline following similar steps described for the synthesis of the (+)-7-([1,2,4]triazolo[1,5-a]pyridin-6-yl)-4-(3,4-dichlorophenyl)-1,2,3,4-tetrahydroisoquinoline, L-tartrate salt ($[\alpha]^{24}_D$-6.0° (c 0.10, methanol)).

Example 2

Alternate Synthesis of Example 1

Step A: To a solution of the triflate (9.5 g, 21.6 mmol) from step G in Example 1 and bis(pinacolato)diboron (6.6 g, 25.9 mmol) in dimethyl sulfoxide (200 mL) was added potassium acetate (6.4 g, 64.8 mmol). The solution was degassed with argon for 5 minutes and then dichloro[1,1'-bis(diphenylphosphino)ferrocene]palladium(II) (1.6 g, 2.2 mmol) was added to it. The reaction mixture was degassed with argon for 5 minutes, heated at 80° C. for 1 hour, and then cooled to room temperature. To this solution were added 6-bromo-[1,2,4]triazolo[1,5-α]pyridine (4.8 g, 23.8 mmol) and an aqueous solution of cesium carbonate (21.1 g, 64.8 mmol in 87 mL of water). The resultant solution was degassed with argon and then dichloro[1,1'-bis(diphenylphosphino)ferrocene]palladium(II) (0.8 g, 1.1 mmol) was added to it. The reaction mixture was degassed with argon and heated at 80° C. for 1 hour. A dark sticky oil formed during the reaction. The dark supernatant solution was poured out, diluted with water, and extracted with ethyl acetate (3×), which was dried over sodium sulfate and concentrated in vacuo. The oil left was dissolved in dichloromethane and the resultant solution was washed with water, dried over sodium sulfate, and concentrated in vacuo. The combined crude product was purified by flash column chromatography (100% ethyl acetate to 92:7.2:0.8 ethyl acetate/methanol/ammonium hydroxide) to give 7-([1,2,4]triazolo[1,5-α]pyridin-6-yl)-4-(3,4-dichlorophenyl)-2-methyl-1,2,3,4-tetrahydroisoquinoline (7.7 g, 87%, AUC HPLC 97.6%) as a brown foam: $^1$H NMR (500 MHz, CDCl$_3$) δ 8.77 (s, 1H), 8.37 (s, 1H), 7.82 (d, J=9.0 Hz, 1H), 7.76 (d, J=9.0 Hz, 1H), 7.39-7.32 (m, 4H), 7.09 (d, J=8.0 Hz, 1H), 7.01 (d, J=8.5 Hz, 1H), 4.26 (t, J=6.5 Hz, 1H), 3.75 (app s, 2H), 3.01 (dd, J=11.5, 5.5 Hz, 1H), 2.64 (dd, J=11.5, 6.5 Hz, 1H), 2.46 (s, 3H).

Step B: To a solution of the 7-([1,2,4]triazolo[1,5-α]pyridin-6-yl)-4-(3,4-dichlorophenyl)-2-methyl-1,2,3,4-tetrahydroisoquinoline (7.2 g, 17.6 mmol) from step A above in 1,2-dichloroethane (180 mL) at 0° C. was added proton sponge (3.8 g, 17.6 mmol), followed by addition of 1-chloroethyl chloroformate (2.3 mL, 21.1 mmol). After the addition, the reaction solution was stirred at 0° C. for 20 minutes and room temperature for 14 hours. Additional 1-chloroethyl chloroformate (0.5 mL, 4.6 mmol) was added to the reaction solution. The reaction solution was stirred for another 3 hours and then it was cooled to 0° C., washed with aqueous hydrochloric acid (1N). Precipitate formed during the acid wash. The organic extract was separated, dried over sodium sulfate, and concentrated in vacuo. The residue obtained was purified by flash column chromatography (dichloromethane to 95:4.5:0.5 dichloromethane/methanol/ammonium hydroxide) to give two batches of partially purified carbamate intermediates, which were dissolved in methanol and refluxed for 1 hour. The reaction solutions were concentrated in vacuo and the crude product obtained was purified by a combination of flash column chromatography (ethyl acetate to 88:10.2:0.8 ethyl acetate/methanol/ammonium hydroxide) and preparative thin layer chromatography (ethyl acetate/methanol/ammonium hydroxide 90:9:1) to give the desired des-methyl tetrahydroisoquinoline (3.8 g, 54%; AUC HPLC 98.7%) as a light pink foam: $^1$H NMR (500 MHz, CDCl$_3$) δ 8.78-8.77 (m, 1H), 8.37 (s, 1H), 7.83 (dd, J=9.5, 1.0 Hz, 1H), 7.77 (dd, J=9.0, 1.5 Hz, 1H), 7.39 (d, J=8.5 Hz, 1H), 7.36-7.26 (m, 3H), 7.05-7.00 (m, 2H), 4.24 (d, J=16.5 Hz, 1H), 4.17 (d, J=16.5 Hz, 1H), 4.13-4.11 (m, 1H), 3.44 (dd, J=12.5, 5.0 Hz, 1H), 3.11 (dd, J=13.0, 6.0 Hz, 1H).

Step C: To a solution of des-methyl tetrahydroisoquinoline (3.75 g, 9.48 mmol) from step B above in ethanol (80 mL) was added activated carbon (3.0 g) and stirred at room temperature for 30 minutes. The carbon was removed by filtration and the filtrate obtained was concentrated in vacuo. The resultant oil was dissolved in ethanol (60 mL) and a solution of L-tartaric acid (1.44 g, 9.5 mmol) in ethanol (20 mL) was added. Upon which, white precipitate formed immediately. The slurry was stirred at room temperature for 10 minutes and filtered. The cake obtained was stirred in hot ethanol (70° C.) for 3 hours and filtered. The cake obtained was dried in vacuo at 50-60° C. for 40 hours to give the (+)-7-([1,2,4]triazolo[1,5-α]pyridin-6-yl)-4-(3,4-dichlorophenyl)-1,2,3,4-tetrahydroisoquinoline L-tartrate (3.7 g, 73%; AUC HPLC 99.4% at 250 nm) as an off-white solid $[α]^{23}{}_D$+16.8° (c 0.13, methanol): $^1$H NMR (500 MHz, CD$_3$OD) δ 9.09 (s, 1H), 8.53 (s, 1H), 8.02 (dd, J=9.0; 2.0 Hz, 1H), 7.86 (d, J=9.0 Hz, 1H), 7.68 (s, 1H), 7.64-7.61 (m, 1H), 7.55 (d, J=8.0 Hz, 1H), 7.48 (d, J=2.0 Hz, 1H), 7.24 (dd, J=8.0; 2.0 Hz, 1H), 7.04 (d, J=8.0 Hz, 1H), 4.65-4.57 (m, 2H), 4.52 (d, J=16.0 Hz, 1H), 4.41 (s, 2H), 3.79 (dd, J=12.5; 6.0 Hz, 1H), 3.44 (t, J=12.5 Hz, 1H). ESI MS m/z 395 [M+H]$^+$ Anal. Calcd. for C$_{21}$H$_{16}$Cl$_2$N$_4$·C$_4$H$_6$O$_6$·0.5H$_2$O: C, 54.16; H, 4.18; N, 10.11. Found: C, 53.96; H, 3.98; N, 9.94.

Example 3

Alternative Synthesis of Example 1 (Hydrochloride)

Step A: To a 1 L round-bottom flask was added 2-amino-5-bromopyridine (100 g, 578 mmol), DMF-DMA (101 mL, 751 mmol) and 2-propanol (200 mL). The mixture was heated to reflux for 3 h to give a clear dark solution. It was then cooled to 50° C. and hydroxylamine hydrochloride (52.2 g, 751 mmol) was added. The mixture was stirred at 50° C. overnight to give a yellow suspension. The precipitate was collected by filtration. The black filtrate was concentrated and the residue was stirred in EtOH (20 mL) for 20 min. The solid was collected by filtration. The combined solids were dried in an oven to give N-(5-bromopyridin-2-yl)-N'-hydroxyformimidamide as a sandy solid (94 g, 75% yield).

Step B: N-(5-bromopyridin-2-yl)-N'-hydroxyformimidamide was dissolved in THF (1 L). To the solution at 10° C. was added trifluoroacetic anhydride (106 mL, 751 mmol) slowly to control the reaction temperature below 20° C. After the addition was complete, the mixture was warmed to room temperature and stirred for 2 h. After the reaction was finished, it was quenched with Na$_2$CO$_3$ aqueous solution to adjust pH>7. The organic solvent was removed under reduced pressure, and the product was then extracted with DCM (4×300 mL). The combined organic layers were dried over Na$_2$SO$_4$ and concentrated to dryness. The residue was stirred in ethyl ether (100 mL) and the product 6-bromo-[1,2,4]triazolo[1,5-a]pyridine was collected by filtration as an off-white solid (50 g, 58% yield).

Step C: To a mixture of 3-formylphenylboronic acid (21.41 g, 143 mmol), 6-bromo-[1,2,4]triazolo[1,5-a]pyridine (28.27 g, 143 mmol) in DMSO (600 mL) and water (50 mL) was added Pd(dppf)Cl$_2$ (5.83 g, 7.14 mmol) and Cs$_2$CO$_3$ (116 g, 357 mmol). The reaction temperature reached 45° C. after the addition. HPLC showed that starting materials were consumed after 15 min. The reaction was diluted with water (400 mL). The black precipitate was collected by filtration and dissolved in DCM (300 mL), and washed with brine (200 mL). The aqueous layer was back extracted with DCM (100 mL). The combined organic layers were filtered through a Celite pad and the filtrate was concentrated to give a black solid mixture. The product was recrystallized in methanol to give 3-([1,2,4]triazolo[1,5-a]pyridin-6-yl)benzaldehyde (27.4 g, 123 mmol, 86% yield) as a pale grey solid: m/z=224.0 [M+1]; $^1$H NMR (400 MHz, DMSO-D6) δ ppm 7.74 (t, J=7.68 Hz, 1 H), 7.91-8.02 (m, 2 H), 8.11 (dd, J=9.19, 1.89 Hz, 1 H), 8.17 (d, J=7.81 Hz, 1 H), 8.36 (s, 1 H), 8.57 (s, 1 H), 9.45 (s, 1 H), 10.11 (s, 1 H).

Step D: A mixture of α-bromo-3,4'-dichloroacetophenone (26.7 g, 100 mmol), hexamethylenetetramine (HMTA) (13.97 g, 100 mmol) and NaI (0.5 g) was stirred at room temperature overnight. HPLC analysis indicated consumption of starting materials. The ammonium intermediate was collected by filtration as a white solid, washed with acetone and dried (36 g, 89% yield).

To a solution of the intermediate (36 g, 88 mmol) in EtOH (500 mL) was added 12 N HCl (75 mL, 0.9 mol). The mixture was stirred at 76° C. overnight, and then cooled to room temperature. The product 2-amino-1-(3,4-dichlorophenyl)ethanone hydrochloride was obtained as a crystal solid by filtration (20.2 g, 95% yield): $^1$H NMR (400 MHz, DMSO-D6) 8 ppm 4.62 (s, 2 H), 7.79-7.94 (m, 1 H), 7.98 (dd, J=8.56, 2.01 Hz, 1 H), 8.26 (d, J=2.01 Hz, 1 H), 8.48 (s, 3 H).

Step E: To a solution of 2-amino-1-(3,4-dichlorophenyl)ethanone hydrochloride (50 g, 208 mmol) in MeOH (200 mL) was added sodium borohydride (7.86 g, 208 mmol) at 0° C. slowly. HPLC indicated 100% conversion after 10 min. A solution of 3-([1,2,4]triazolo[1,5-a]pyridin-6-yl)benzaldehyde (46.4 g, 208 mmol) in DCM/MeOH (180 mL/50 mL) was added to the previous solution in one portion at room temperature. The mixed solution was stirred at RT for 2 h, then sodium borohydride (7.86 g, 208 mmol) was added. HPLC indicated 100% conversion after 10 min. Most of the solvent was removed and the residual was dissolved in DCM/NH$_4$OH (4N) (1 L/1 L). The organic layer was washed with brine, dried over Na$_2$SO$_4$, and concentrated to ~250 mL. The product 2-(3-([1,2,4]triazolo[1,5-a]pyridin-6-yl)benzylamino)-1-(3,4-dichlorophenyl)ethanol in DCM solution was used in the next step without further purification (HPLC area 92%): m/z=413.1 [M+1]; $^1$H NMR (400 MHz, CHLOROFORM-D) 8 ppm 2.72 (dd, J=12.21, 8.69 Hz, 1 H), 2.96 (dd, J=12.34, 3.53 Hz, 1 H), 3.85-3.98 (m, 2 H), 4.69 (dd, J=8.56, 3.53 Hz, 1 H), 7.18 (dd, J=8.31, 1.76 Hz, 1 H), 7.34-7.42 (m, 2 H), 7.43-7.56 (m, 4 H), 7.72-7.88 (m, 2 H), 8.36 (s, 1 H), 8.78 (s, 1 H).

Step F: A solution of concentrated sulfuric acid (500 g, 5.0 mol) in a 3 L round bottom flask was cooled to 0° C. with an ice bath. To the flask was added dropwise a solution of 2-(3-([1,2,4]triazolo[1,5-a]pyridin-6-yl)benzylamino)-1-(3,4-dichlorophenyl)ethanol (79 g, 0.191 mol) in DCM (250 mL). The addition was finished in 30 min and the reaction temperature was controlled in the range of 10-20° C. DCM was blown away with nitrogen gas during the addition. The evaporation of DCM helped to lower the reaction temperature. The mixture solution was stirred at RT overnight. HPLC indicated no remaining starting material. The HPLC area ratio of 7-([1,2,4]triazolo[1,5-a]pyridin-6-yl)-4-(3,4-dichlorophenyl)-1,2,3,4-tetrahydroisoquinoline and 5-([1,2,4]triazolo[1,5-a]pyridin-6-yl)-4-(3,4-dichlorophenyl)-1,2,3,4-tetrahydroisoquinoline was 75:25. The reaction mixture was cooled to 0° C. Isopropanol (2 L) was added to the solution slowly, maintaining temperature <0° C. The solid (desired isomer 92% purity) was obtained by filtration. The solid was then dissolved in AcOEt (1 L) and the pH adjusted to 10 with NH$_4$OH. The water layer was extracted with EtOAc twice. The combined organic layers were washed with water, dried over Na$_2$SO$_4$ and concentrated. The residue was dissolved in EtOH (250 mL) and then 1.1 eq of methanesulfonic acid (20.20 g, 0.21 mol) was added and the solution stirred overnight. The resulting precipitate methanesulfonic acid salt (98% purity) was filtered. This was dissolved in water and the pH adjusted with NH$_4$OH to 10, then extracted with AcOEt twice. The combined extracts were washed with water and dried over Na$_2$SO$_4$. After removal of solvent, 7-([1,2,4]triazolo[1,5-a]pyridin-6-yl)-4-(3,4-dichlorophenyl)-1,2,3,4-tetrahydroisoquinoline 7-([1,2,4]triazolo[1,5-a]pyridin-6-yl)-4-(3,4-dichlorophenyl)-1,2,3,4-tetrahydroisoquinoline was obtained in an amorphous state (40.8 g, 54% yield): m/z=395.0 [M+1]; $^1$H NMR (400 MHz, CHLOROFORM-D) 8 ppm 3.05 (dd, J=12.00, 8.00 Hz, 1 H), 3.40 (dd, J=12.00, 4.00 Hz, 1 H), 4.05-4.25 (m, 3H), 6.96 (m, 2 H), 7.25-7.35 (m, 4 H), 7.70-7.80 (m, 2 H), 8.32 (s, 1H), 8.74 (s, 1 H).

Step G: To a solution of 7-([1,2,4]triazolo[1,5-a]pyridin-6-yl)-4-(3,4-dichlorophenyl)-1,2,3,4-tetrahydroisoquinoline (25.2 g, 63.8 mmol) in DMF (30 ml) was added di-tert-butyl dicarbonate (13.91 g, 63.8 mmol). The reaction mixture was stirred at RT for 1 h, then AcOEt (500 ml) was added. The solution was washed with brine and water. The organic layer was dried over Na$_2$SO$_4$. After removal of solvent, solid rac-tert-butyl 7-([1,2,4]triazolo[1,5-a]pyridin-6-yl)-4-(3,4-dichlorophenyl)-3,4-dihydroisoquinoline-2(1H)-carboxylate (30.6 g, 61.8 mmol, 97% yield) was obtained by recrystallization from MeOH; m/z=495.1 [M+1]; $^1$H NMR (400 MHz, CHLOROFORM-D) 8 ppm 1.30 (s, 9H), 3.60-4.15 (m, 3 H), 4.40-5.10 (m, 2H), 6.84-7.05 (m, 2H), 7.13 (d, J=1.51 Hz, 1H), 7.35 (m, 3H), 7.78 (dd, J=8.31, 1.77 Hz, 2 H), 8.31 (s, 1H), 8.72 (s, 1H).

Step H: Chiral SFC separation on a Chiralpak AS-H column (3×25 cm, 5 µm; eluent: CO2/(MeOH/TEA=100/0.2 (v/v))=75/25; 220 nm) yielded (+)-tert-butyl 7-([1,2,4]triazolo[1,5-a]pyridin-6-yl)-4-(3,4-dichlorophenyl)-3,4-dihydroisoquinoline-2(1H)-carboxylate (99.7% ee).

Step I: To a solution of the (+)-enantiomer from Step H (32.41 g, 65.43 mmol) in DCM (150 ml) was added hydrogen chloride-EtOH solution (2.5N, 250 mL) and EtOH 500 mL. The reaction mixture was stirred at 70° C. for 2 h. After removal of the solvent, the residue was refluxed in 1000 ml AcOEt for 1 h. The product (+)-7-([1,2,4]triazolo[1,5-a]pyridin-6-yl)-4-(3,4-dichlorophenyl)-1,2,3,4-tetrahydroisoquinoline hydrochloride (27.4 g, 97% yield) was obtained after filtration and drying. m/z=395.1 [M+1]; $^1$H NMR (400 MHz, DMSO-d$_6$) δ ppm 3.70 (m, 2H), 4.40-4.65 (m, 3H), 6.90 (d, 7.80 Hz, 1H), 7.35 (dd, J=7.8, 2 Hz, 1H), 7.68 (m, 4H), 8.58 (s, 1H), 9.38 (s, 1H), 9.8 (bs, 2H).

Example 4

Primary Binding Assay

Preparation of Membranes

Recombinant HEK-293 cells expressing either the hSERT, hDAT, or hNET proteins were harvested from T-175 flasks as follows. The medium was removed from the flasks and the cells rinsed with HBSS without Ca and without Mg. The cells were then incubated for 5-10 minutes in 10 mM Tris-Cl, pH 7.5, 5 mM EDTA before the cells were lifted with a combination of pipetting and scraping, as needed. The cell suspension was collected into centrifuge bottles and homogenized for 30 seconds with a Polytron homogenizer. The suspension was centrifuged for 30 minutes at 32,000×g, 4° C. The supernatant was decanted and the pellet resuspended and homogenized in 50 mM Tris-Cl, pH 7.5, 1 mM EDTA for 10 seconds. The suspension was then centrifuged again for 30 minutes at 32,000×g, 4° C. The supernatant was decanted and the pellet resuspended in 50 mM Tris-Cl, pH 7.5, 1 mM EDTA and briefly homogenized. A Bradford assay (Bio-rad) was performed and the membrane preparation diluted to 2 mg/ml with 50 mM Tris-Cl, pH 7.5, 1 mM EDTA. Aliquots were prepared, and then frozen and stored at −80° C.

SERT Radioligand Binding Assay

Compounds were dissolved in 100% DMSO at a concentration 100 times the desired highest assay concentration, serially diluted 1:3 in 100% DMSO, and 0.4 µl/well of each solution was dispensed to a Nunc polypropylene, round bottom, 384-well plate. 100% inhibition is defined with 0.4 µl/well of 1 mM fluoxetine dissolved in DMSO. 20 µl/well of a 2× membrane preparation (15 ug/ml in 50 mM Tris-Cl, pH 7.5, 120 mM NaCl, 5 mM KCl) and 20 µl/well of a 2× radioligand solution (520 pM [$^{125}$I]RTI-55 in 50 mM Tris-Cl, pH 7.5, 120 mM NaCl, 5 mM KCl) were added to each well and the reaction incubated for 1 hour at room temperature.

The contents of the assay plate were then transferred to a Millipore Multiscreen$_{HTS}$ GF/B filter plate which was pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing were completed in less than 90 seconds. The plates were air-dried overnight, 12 µl/well of MicroScint scintillation fluid added, and the plates counted in a Trilux.

DAT Radioligand Binding Assay

Compounds were dissolved in 100% DMSO at a concentration 100 times the desired highest assay concentration, serially diluted 1:3 in 100% DMSO, and 0.4 µl/well of each solution was dispensed to a Nunc polypropylene, round bottom, 384-well plate. 100% inhibition is defined with 0.4 µl/well of 1 mM GBR-12935 dissolved in DMSO. 20 ul/well of a 2× membrane preparation (12.5 µg/ml in 30 mM sodium phosphate buffer, pH 7.9 at 4° C.) and 20 µl/well of a 2× radioligand solution (250 µM [$^{125}$I]RTI-55 in 30 mM sodium phosphate buffer, pH 7.9 at 4° C.) were added to the well and the reaction incubated for 1 hour at room temperature. The contents of the assay plate were then transferred to a Millipore Multiscreen$_{HTS}$ GF/B filter plate which was pretreated with 0.5% PEI for at least one hour. The plate was vacuum-filtered and washed with 7 washes of 100 µl/well 50 mM Tris-Cl, pH 7.5, 120 mM NaCl, 5 mM KCl chilled to 4° C. The filtration and washing were completed in less than 90 seconds. The plates were air-dried overnight, 12 µl/well of MicroScint scintillation fluid added, and the plates counted in a Trilux.

NET Radioligand Binding Assay

Compounds were dissolved in 100% DMSO at a concentration 100 times the desired highest assay concentration, serially diluted 1:3 in 100% DMSO, and 1.0 µl/well of each solution was dispensed to a Nunc polypropylene, round bottom, 384-well plate. 100% inhibition is defined with 1.0 µl/well of 10 mM desipramine dissolved in DMSO. 50 µl/well of a 2× membrane preparation (0.4 mg/ml in 50 mM Tris-Cl, pH 7.5, 120 mM NaCl, 5 mM KCl) and 50 µl/well of a 2× radioligand solution (4 nM [$^3$H]nisoxetine in 50 mM Tris-Cl, pH 7.5, 120 mM NaCl, 5 mM KCl) were added to the well and the reaction incubated for 1 hour at room temperature. The contents of the assay plate were then transferred to a Millipore Multiscreen$_{HTS}$ GF/B filter plate which was pretreated with 0.5% PEI for at least one hour. The plate was vacuum filtered and washed with 7 washes of 100 µl/well 50 mM Tris-Cl, pH 7.5, 120 mM NaCl, 5 mM KCl chilled to 4° C. The filtration and washing were completed in less than 90 seconds. The plates were air-dried overnight, 12 µl/well of MicroScint scintillation fluid added, and the plates counted in a Trilux.

Data Analysis

The raw data was normalized to percent inhibition using control wells defining 0% (DMSO only) and 100% (selective inhibitor) inhibition which were run on each plate. Each plate was run in triplicate, and the concentration response curve thus generated was fit using the four-parameter dose response equation, $Y = Bottom + (Top - Bottom)/(1 + 10^{((Log\ IC_{50} - X) * HillSlope)})$ in order to determine the $IC_{50}$ value for each compound. The radioligand concentration chosen for each assay corresponds to the $K_d$ concentration determined through saturation binding analysis for each assay.

Example 5

Occupancy Assay

The general procedure for brain tissue collection and transporter occupancy assessment is briefly described as follows. Mice were sacrificed by asphyxiation in $CO_2$, rats by decapitation and dogs by IV injection of euthanasia solution. For mice and rats, after the brains were removed from the skull, the forebrain tissue (removal of the brainstem and cerebellum) was used for SERT, NET, and DAT occupancy assessment. In dogs, the striatum was dissected for DAT occupancy and the remaining forebrain tissue (without the striatum, brainstem, and cerebellum) was used for SERT and NET occupancy assessment. The brain tissues were frozen in chilled isopentane and stored at −80° C. until homogenization.

The brain tissues were thawed and then homogenized using a polytron homogenizer (Kinematica). Sample aliquots were frozen immediately and stored at −80° C. Protein content was measured for each sample using a Coomassie protein assay kit (Pierce).

On the day of ex vivo binding for occupancy assessment, frozen sample aliquots were thawed and needle homogenized, and 100 µg of the tissue was incubated for SERT, NET, and DAT binding under assay conditions summarized in Table 1. After incubation, the reactions were terminated by the addition of ice-cold assay buffer and rapid filtration through a Brandel Cell Harvester using FPXLR-196 filters. The filters were washed twice with ice-cold incubation buffer, punched into a clear plate prior to the addition of 200 ul scintillation fluid per well. Radioligand was measured using a Wallac Microbeta liquid scintillation counter.

TABLE 1

Ex Vivo Binding Assay Conditions for Serotonin, Norepinephrine and Dopamine Transporter Occupancy.

| Transporter | Radioligand | Non-Specific Drug (µM) | Buffer (nM) | Incubation Time and Temperature |
|---|---|---|---|---|
| SERT | 2 nM [$^3$H]Citalopram | Fluoxetine, 10 | Tris, 50 NaCl, 120 KCl, 5 | 10 minutes at 4° C. |
| DAT | 0.1 nM [$^{125}$I]RTI-55 (+0.5 µM citalopram) | GBR-12935, 10 | Sodium phosphate buffer, 30 | 10 minutes 4° C. |
| NET | 5 nM [$^3$H]-Nisoxetine | Reboxetine, 10 | Tris, 50 NaCl, 300 KCl, 5 | 20 minutes at 4° C. |

The specific binding was calculated by subtracting the value of the non-specific binding from that of the total binding in each sample. The percent occupancy was calculated as (1−specific binding in drug treated/specific binding in vehicle treated)×100%. For estimation of in vivo occupancy $EC_{50}$ (total plasma concentration of compound producing 50% occupancy), plots of occupancy values versus plasma concentrations were fitted to a one-site binding model using nonlinear regression according to the following equation: % Occupancy=Emax*C/($EC_{50}$+C) where Emax is the maximal specific binding, C is the drug concentration, and $EC_{50}$ is the total plasma concentration required for 50% binding site occupancy. Nonlinear regression was performed using GraphPad Prism version 3.00 (GraphPad Software, San Diego, Calif.).

The results are shown in Table 2, below:

TABLE 2

IC$_{50}$ and Occupancy Values

| Example | SERT IC50 (nM) | DAT IC50 (nM) | NET IC50 (nM) | SERT Occupancy % | DAT Occupancy % | NET Occupancy % | Dose_mg/kg | time point (hour) |
|---|---|---|---|---|---|---|---|---|
| 1 (+)-enantiomer | 1.8 | 30.8 | 26.0 | 75 | 26 | 11 | 1 | 3 |
| 1 (−)-enantiomer | 4.2 | 104.6 | 4.8 | 41 | 30 | 33 | 1 | 3 |

Example 6

In Vivo Behavioral Assays

For All Tests

All animals were maintained in accordance with the guidelines of the Committee on Animals of the Bristol-Myers Squibb Company and *Guide for Care and Use of Laboratory Animals*, Institute of Animal Laboratory Resources, 1996, which are hereby incorporated by reference in their entirety. Research protocols were approved by the Bristol-Myers Squibb Company Institutional Animal Care and Use Committee.

Mouse Tail Suspension Assay

Male Swiss Webster mice were housed 3-4 per cage in rooms maintained at a constant temperature (21-23° C.) and humidity (50±10%) on a 12-hour light/dark cycle. Animals had ad libitum access to water and food throughout studies. On the day of testing, they were brought into the testing room and allowed to acclimate for 1 hour. To begin testing, the tail was attached to a piece of tape which was then attached to a hook on the ceiling of a sound-attenuated chamber. Immobility was automatically recorded using the Med Associates software. Compounds were administered acutely at a fixed pretreatment interval before session.

The minimum effective dose of Example 1-(+)-enantiomer in the mouse tail suspension study was 10 mg/kg.

Rat Forced Swim Assay

Male Sprague Dawley rats are housed in pairs in rooms maintained at a constant temperature (21-23° C.) and humidity (50±10%) on a 12-hour light/dark cycle. Animals have ad libitum access to water and food throughout studies. Animals are handled for two minutes each on the two days prior to the start of the experiment. On the first day of testing, rats are placed in the swim tank (a Pyrex cylinder 46 cm tall×21 cm in diameter, filled with 30 cm of water ranging between 24-26° C.) for 15 minutes (the pre-swim session). At the end of the 15-minute session, rats are dried and replaced in their home cage. Compounds are administered at three time points in the next 24 hour (23.5, 5, and 1 hour), prior to a second test swim. This swim test is 5 minutes in duration and the animals' behavior is videotaped and active behaviors (immobility, swimming, climbing) are scored. At the end of each 5-second period during the 5-minute test session the rat's behavior is scored as one of the following: immobility (the rat remained floating in the water without struggling and made only those movements necessary to keep its head above water), swimming (the rat made active swimming motions, more than necessary to merely maintain its head above water, e.g., moving around in the cylinder), or climbing (the rat made active movements with its forepaws in and out of the water, usually directed against the cylinder wall). Compounds are only identified by a predesignated code and the experimenter remains blinded throughout the experiment (including while scoring videotapes).

Rat and Mouse Locomotor Activity

Animals are housed according to conditions described above for the two species. The testing apparatus consists of Plexiglas chambers equipped with Digiscan activity monitors (Omnitech Electronics, Columbus, Ohio) that detect interruptions of eight photobeams. Horizontal activity is recorded in 5-minute bins for a total of 60 minutes and expressed as total distance covered (in cm). Compounds are administered acutely at a fixed pretreatment interval prior to testing.

Example 7

Preparation of Single Crystals of (S)-7-([1,2,4]triazolo[1,5-a]pyridin-6-yl)-4-(3,4-dichlorophenyl)-1,2,3,4-tetrahydroisoquinoline L-tartrate (L-tartrate salt)

(S)-7-([1,2,4]triazolo[1,5-a]pyridin-6-yl)-4-(3,4-dichlorophenyl)-1,2,3,4-tetrahydroisoquinoline L-tartrate salt (20 mg) was dissolved in methanol (8 mL) under heating in a vial. Distilled water (2 mL) was then added to the above clear solution. The resulting solution was capped and placed at room temperature. Needle-like crystals of (S)-7-([1,2,4]triazolo[1,5-a]pyridin-6-yl)-4-(3,4-dichlorophenyl)-1,2,3,4-tetrahydroisoquinoline L-tartrate salt were obtained after slow evaporation in air within days.

Example 8

Preparation of Single Crystals of (S)-7-([1,2,4]triazolo[1,5-a]pyridin-6-yl)-4-(3,4-dichlorophenyl)-1,2,3,4-tetrahydroisoquinoline monohydrochloride monoisopropanolate monohydrate (HCl salt; Form SA-1)

(S)-7-([1,2,4]triazolo[1,5-a]pyridin-6-yl)-4-(3,4-dichlorophenyl)-1,2,3,4-tetrahydroisoquinoline mono-HCl salt (20 mg) was dissolved in isopropanol (10 mL) under heating in a vial. Distilled water (2 mL) was then added to the above clear solution. The resulting solution was capped and placed at room temperature. Long needle crystals of (S)-7-([1,2,4]triazolo[1,5-a]pyridin-6-yl)-4-(3,4-dichlorophenyl)-1,2,3,4-tetrahydroisoquinoline mono-HCl monoisopropanolate monohydrate salt were obtained after slow evaporation in air within days. The needle-like crystals were separated from mother liquor by filtration and the wet cake was dried in an oven for 16 hours under the condition of 45° C. and 100 mmHg.

Example 9

Preparation of Single Crystals of (S)-7-([1,2,4]triazolo[1,5-a]pyridin-6-yl)-4-(3,4-dichlorophenyl)-1,2,3,4-tetrahydroisoquinoline monohydrochloride (HCl salt; Form N-2)

(S)-7-([1,2,4]triazolo[1,5-a]pyridin-6-yl)-4-(3,4-dichlorophenyl)-1,2,3,4-tetrahydroisoquinoline mono-HCl salt (20 mg) was dissolved in methanol (8 mL) under heating in a vial. Distilled water (2 mL) was then added to the above clear solution. The resulting solution was capped and placed at room temperature. Needle like single crystals of (S)-7-([1,2,4]triazolo[1,5-a]pyridin-6-yl)-4-(3,4-dichlorophenyl)-1,2,3,4-tetrahydroisoquinoline mono-HCl salt were obtained after slow evaporation in air within days.

Example 10

Single Crystal Analysis by X-Ray Crystallography

The data of (S)-7-([1,2,4]triazolo[1,5-a]pyridin-6-yl)-4-(3,4-dichlorophenyl)-1,2,3,4-tetrahydroisoquinoline L-tartrate (L-tartrate salt) and (S)-7-([1,2,4]triazolo[1,5-a]pyridin-6-yl)-4-(3,4-dichlorophenyl)-1,2,3,4-tetrahydroisoquinoline monohydrochloride (HCl salt; Form N-2) crystals were collected on a SMART CCD diffractometer equipped with graphite-monochromated Cu Kα radiation (λ=1.54178 Å) at 225K and the room temperature, respectively. The data of (S)-7-([1,2,4]triazolo[1,5-a]pyridin-6-yl)-4-(3,4-dichlorophenyl)-1,2,3,4-tetrahydroisoquinoline monohydrochloride monoisopropanolate monohydrate (HCl salt; Form SA-1) were collected on an X8-ApexII diffractometer equipped with graphite-monochromated Cu Kα radiation (λ=1.54178 Å) at room temperature (APEX-II 1.0-28, Data Collection Software for Bruker CCD devices. Bruker AXS Inc., Madison, Wis., US. SAINT PLUS, Processing Software for BrukerCCD devices, Bruker AXS Inc., Madison, Wis., US). The final unit cell parameters were determined using the entire data set.

All structures were solved by direct methods and refined by the full-matrix least-squares techniques, using the SHELXTL software package (Sheldrick, G M. 1997, SHELXTL. Structure Determination Programs. Version 5.10, Bruker AXS, Madison, wisconsin, USA.). The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)_2/\Sigma_w|F_o|^2]^{1/2}$, where w is an appropriate weighting function based on errors in the observed intensities. Difference Fourier maps were examined at all stages of refinement. In L-tartrate form, one of chloro atoms on pendant phenyl ring is disordered over two positions with 50% occupancy ratio each. The tartaric acid molecule is also disordered, which could not be modeled well. The numbers of methanol molecules could not be identified due to disorder. All non-hydrogen atoms were refined with anisotropic thermal displacement parameters. The hydrogen atoms associated with hydrogen bonding were located in the final difference Fourier maps while the positions of the other hydrogen atoms were calculated from an idealized geometry with standard bond lengths and angles. They were assigned isotropic temperature factors and included in structure factor calculations with fixed parameters.

The crystal data of the L-tartrate salt form is shown in Table 3 and the fractional atomic coordinates are listed in Table 4. The crystal data of Form SA-1 is shown in Table 5 and the fractional atomic coordinates are listed in Table 6. The crystal data of Form N-2 is shown in Table 7 and the fractional atomic coordinates are listed in Table 8. It should be understood by one of ordinary skills in the art that slight variations in the coordinates are possible and are considered to be within the scope the present disclosure.

TABLE 3

Crystal Data of L-tartrate Form

| | |
|---|---|
| Empirical formula | C40H40Cl2N8O8 |
| Formula weight | 831.70 |
| Temperature | 225(1) K |
| Wavelength | 1.54178 Å |
| Crystal system, space group | Orthorhombic, C222$_1$ |
| Unit cell dimensions | a = 7.6264(10) Å   alpha = 90 deg. |
| | b = 38.942(5) Å   beta = 90 deg. |
| | c = 24.449(3) Å   gamma = 90 deg. |
| Volume | 7261.1(16) Å$^3$ |
| Z, Calculated density | 8, 1.522 Mg/m$^3$ |
| Absorption coefficient | 2.195 mm$^{-1}$ |
| F(000) | 3472 |
| Theta range for data collection | 2.27 to 66.20 deg. |
| Limiting indices | -8 <= h <= 8, -45 <= k <= 42, |
| | -22 <= l <= 28 |
| Reflections collected/unique | 24815/6156 [R(int) = 0.1027] |
| Refinement method | Full-matrix least-squares on F^2 |
| Data/restraints/parameters | 6156/2/323 |
| Goodness-of-fit on F^2 | 2.340 |
| Final R indices [I > 2sigma(I)] | R1 = 0.2345, wR2 = 0.4418 |
| R indices (all data) | R1 = 0.3127, wR2 = 0.4595 |
| Absolute structure parameter | 0.00(11) |
| Extinction coefficient | 0.0075(9) |
| Largest diff. peak and hole | 0.991 and -0.773 e. Å$^{-3}$ |

TABLE 4

Atomic Coordinates of L-tartrate Form
Atomic coordinates (×10$^4$) and equivalent isotropic displacement parameters (Å$^2$ × 10$^3$) for L-tartrate Form. U(eq) is defined as one third of the trace of the orthogonalized Uij tensor.

| | x | y | z | U(eq) |
|---|---|---|---|---|
| Cl(1) | 8174(9) | 94(1) | 4057(2) | 171(2) |
| Cl(2') | 5256(12) | -323(2) | 4561(3) | 137(3) |
| Cl(2) | 11696(16) | -83(2) | 4303(4) | 201(6) |
| C(1) | 8480(30) | -296(3) | 4374(6) | 109(5) |
| C(2) | 10110(40) | -377(4) | 4452(8) | 149(8) |
| C(3) | 10610(20) | -698(5) | 4682(7) | 136(6) |
| C(4) | 9280(20) | -919(2) | 4902(4) | 78(3) |
| C(5) | 7540(20) | -803(3) | 4839(5) | 107(4) |
| C(6) | 7210(20) | -477(3) | 4556(5) | 109(5) |
| C(7) | 9651(19) | -1252(2) | 5194(5) | 97(4) |
| C(8) | 8790(20) | -1532(3) | 4886(5) | 122(5) |
| C(9) | 7840(20) | -1835(2) | 5751(6) | 111(5) |
| C(10) | 8275(16) | -1504(3) | 6055(6) | 87(3) |
| C(11) | 9041(16) | -1238(2) | 5781(5) | 83(3) |
| C(12) | 9409(14) | -941(2) | 6125(5) | 71(3) |
| C(13) | 8887(15) | -937(3) | 6658(6) | 82(3) |
| C(14) | 8050(16) | -1194(3) | 6915(5) | 75(3) |
| C(15) | 7808(18) | -1500(2) | 6586(6) | 90(4) |
| C(16) | 7563(15) | -1182(2) | 7472(6) | 79(3) |
| C(17) | 6993(17) | -875(4) | 7699(6) | 96(4) |
| C(18) | 6487(18) | -1113(4) | 8577(8) | 100(4) |
| C(19) | 7058(19) | -1442(5) | 8390(5) | 112(5) |
| C(20) | 7492(19) | -1472(3) | 7861(7) | 118(5) |
| C(21) | 5610(30) | -748(9) | 8994(6) | 194(13) |
| C(22) | 7820(20) | -2663(4) | 4481(6) | 124(4) |
| O(3) | 10030(30) | -2275(4) | 4338(6) | 225(7) |
| C(23) | 9000(20) | -2557(4) | 4090(6) | 119(4) |
| O(2) | 7170(20) | -2487(3) | 4903(5) | 170(4) |
| O(1) | 7230(20) | -2972(3) | 4484(5) | 186(5) |
| N(1) | 8830(20) | -1870(2) | 5245(6) | 138(5) |
| N(2) | 6491(14) | -849(3) | 8247(6) | 109(4) |
| N(3) | 5890(20) | -1046(6) | 9099(9) | 150(7) |
| N(4) | 5882(18) | -566(3) | 8552(6) | 119(4) |
| O(8) | -840(20) | 53(4) | 2431(8) | 235(7) |
| O(1W) | 9327(17) | -3528(3) | 4909(5) | 175(4) |
| C(74) | 450(50) | -1233(9) | 3340(13) | 272(14) |
| O(9) | -2350(140) | -964(16) | 3320(30) | 630(40) |
| O(4) | 7600(60) | -2153(9) | 3690(14) | 400(15) |
| O(6) | 10620(40) | -2645(6) | 3106(9) | 291(9) |
| C(72) | -2920(80) | -1321(14) | 3380(20) | 400(30) |
| O(7) | -160(50) | -761(8) | 3131(12) | 351(13) |

TABLE 4-continued

Atomic Coordinates of L-tartrate Form
Atomic coordinates (×10$^4$) and equivalent isotropic displacement parameters (Å$^2$ × 10$^3$) for L-tartrate Form. U(eq) is defined as one third of the trace of the orthogonalized Uij tensor.

|  | x | y | z | U(eq) |
|---|---|---|---|---|
| C(70) | −300(120) | −361(12) | 2710(20) | 420(30) |
| C(25) | 9840(80) | −2305(16) | 3320(20) | 440(30) |
| O(5) | 8080(40) | −2558(7) | 2969(9) | 312(11) |
| C(24) | 8360(40) | −2552(8) | 3522(10) | 241(11) |
| H(3A) | 11778 | −764 | 4690 | 164 |
| H(5A) | 6612 | −931 | 4976 | 128 |
| H(7A) | 10920 | −1291 | 5191 | 116 |
| H(8A) | 9408 | −1570 | 4544 | 146 |
| H(8B) | 7592 | −1469 | 4803 | 146 |
| H(9A) | 8097 | −2030 | 5986 | 133 |
| H(9B) | 6598 | −1839 | 5669 | 133 |
| H(12A) | 10003 | −753 | 5980 | 85 |
| H(13A) | 9130 | −740 | 6861 | 99 |
| H(15A) | 7325 | −1695 | 6744 | 108 |
| H(17A) | 6943 | −680 | 7479 | 115 |
| H(19A) | 7126 | −1628 | 8627 | 134 |
| H(20A) | 7766 | −1689 | 7730 | 142 |
| H(21A) | 5111 | −624 | 9280 | 233 |
| H(1A) | 8376 | −2045 | 5049 | 166 |
| H(1B) | 9947 | −1923 | 5325 | 166 |

TABLE 5

Crystal Data of HCl salt: Form SA-1

| | |
|---|---|
| Empirical formula | C24H26Cl3N4O2 |
| Formula weight | 508.84 |
| Temperature | 298(2) K |
| Wavelength | 1.54178 Å |
| Crystal system, space group | Monoclinic, P2$_1$ |
| Unit cell dimensions | a = 11.0668(9) Å   alpha = 90 deg. |
| | b = 7.3750(6) Å   beta = 100.594(7) deg. |
| | c = 15.3927(14) Å   gamma = 90 deg. |
| Volume | 1234.90(18) Å$^3$ |
| Z, Calculated density | 2, 1.363 Mg/m$^3$ |
| Absorption coefficient | 3.595 mm$^{-1}$ |
| F(000) | 530 |
| Theta range for data collection | 4.06 to 61.98 deg. |
| Limiting indices | −12 <= h <= 12, −7 <= k <= 6, −17 <= l <= 15 |
| Reflections collected/unique | 3911/2687 [R(int) = 0.0253] |
| Completeness to theta = 61.98 | 89.5% |
| Refinement method | Full-matrix least-squares on F$^2$ |
| Data/restraints/parameters | 2687/1/306 |
| Goodness-of-fit on F$^2$ | 1.035 |
| Final R indices [I > 2sigma(I)] | R1 = 0.0382, wR2 = 0.0994 |
| R indices (all data) | R1 = 0.0423, wR2 = 0.1027 |
| Absolute structure parameter | 0.02(2) |
| Largest diff. peak and hole | 0.270 and −0.201 e.Å$^{-3}$ |

TABLE 6

Atomic Coordinates of HCl salt: Form SA-1
Atomic coordinates (×10$^4$) and equivalent isotropic displacement parameters Å$^2$ × 10$^3$ for Form SA-1. U(eq) is defined as one third of the trace of the orthogonalized Uij tensor.

|  | x | y | z | U(eq) |
|---|---|---|---|---|
| Cl | 12265(1) | 6142(1) | 1683(1) | 49(1) |
| Cl(1) | 7875(1) | 12955(2) | 4765(1) | 82(1) |
| Cl(2) | 8143(1) | 9869(2) | 6212(1) | 87(1) |
| N(1) | 2603(2) | 8917(4) | −585(2) | 34(1) |
| N(2) | 10328(2) | 9284(4) | 1422(2) | 39(1) |
| C(3) | 7992(3) | 8350(5) | 1854(2) | 31(1) |
| C(4) | 6974(3) | 8951(5) | 360(2) | 32(1) |
| N(5) | 1421(3) | 9376(5) | −494(2) | 47(1) |
| C(6) | 5842(3) | 8414(5) | 549(2) | 32(1) |
| C(7) | 4724(3) | 8458(5) | −145(2) | 32(1) |
| C(8) | 8036(3) | 8902(5) | 998(2) | 31(1) |
| C(9) | 3613(3) | 8927(5) | 63(2) | 36(1) |
| C(10) | 9143(3) | 8296(5) | 2564(2) | 35(1) |
| N(11) | 1476(3) | 8685(5) | −1929(2) | 51(1) |
| C(12) | 5807(3) | 7820(6) | 1405(2) | 37(1) |
| C(13) | 8878(3) | 8695(5) | 3475(2) | 37(1) |
| C(14) | 6859(3) | 7787(6) | 2035(2) | 38(1) |
| C(15) | 4772(3) | 8039(5) | −1033(2) | 41(1) |
| C(16) | 10107(3) | 9607(5) | 2333(2) | 38(1) |
| C(17) | 2614(3) | 8532(5) | −1448(3) | 39(1) |
| C(18) | 9221(3) | 9458(6) | 715(2) | 42(1) |
| C(19) | 8304(4) | 10787(6) | 4526(3) | 47(1) |
| C(20) | 8550(3) | 10430(5) | 3699(3) | 42(1) |
| C(21) | 3747(4) | 8064(6) | −1674(2) | 46(1) |
| C(22) | 821(3) | 9193(6) | −1314(3) | 50(1) |
| C(23) | 8957(4) | 7332(6) | 4108(3) | 48(1) |
| C(24) | 8714(4) | 7701(7) | 4937(3) | 55(1) |
| C(25) | 8399(4) | 9426(8) | 5162(3) | 58(1) |
| OW1 | 12197(4) | 11835(6) | 1559(3) | 63(1) |
| O(01) | 13401(5) | 9513(6) | 2783(4) | 138(2) |
| C(01) | 14893(7) | 7959(17) | 3801(5) | 166(5) |
| C(02) | 14430(8) | 9598(14) | 3370(6) | 139(3) |
| C(03) | 14517(9) | 11360(20) | 3818(8) | 221(8) |
| H(2A) | 10639 | 8162 | 1397 | 46 |
| H(2B) | 10900 | 10076 | 1311 | 46 |
| H(4A) | 7017 | 9351 | −207 | 38 |
| H(9A) | 3554 | 9248 | 638 | 43 |
| H(10A) | 9484 | 7068 | 2573 | 42 |
| H(12A) | 5066 | 7445 | 1549 | 44 |
| H(14A) | 6817 | 7377 | 2600 | 46 |
| H(15A) | 5524 | 7738 | −1183 | 49 |
| H(16A) | 9829 | 10844 | 2381 | 45 |
| H(16B) | 10871 | 9453 | 2750 | 45 |
| H(18A) | 9335 | 8717 | 216 | 50 |
| H(18B) | 9148 | 10709 | 518 | 50 |
| H(20A) | 8495 | 11359 | 3285 | 50 |
| H(21A) | 3795 | 7776 | −2255 | 55 |
| H(22A) | −20 | 9407 | −1461 | 60 |
| H(23A) | 9175 | 6163 | 3970 | 58 |
| H(24A) | 8763 | 6773 | 5351 | 66 |
| HW1 | 12650(50) | 11440(80) | 1990(40) | 67(19) |
| HW2 | 12190(50) | 12930(110) | 1710(40) | 90(20) |
| H(01D) | 13362 | 8533 | 2528 | 207 |
| H(01A) | 14782 | 6981 | 3382 | 249 |
| H(01B) | 14456 | 7696 | 4270 | 249 |
| H(01C) | 15752 | 8098 | 4041 | 249 |
| H(02A) | 15024 | 9777 | 2977 | 167 |
| H(03A) | 14198 | 12289 | 3401 | 331 |
| H(03B) | 15361 | 11617 | 4062 | 331 |
| H(03C) | 14047 | 11331 | 4284 | 331 |

TABLE 7

Crystal Data of HCl salt: Form N-2

| | |
|---|---|
| Empirical formula | C21H17Cl3N4 |
| Formula weight | 431.74 |
| Temperature | 298(2) K |
| Wavelength | 1.54178 Å |
| Crystal system, space group | Orthorhombic, P2$_1$2$_1$2$_1$ |
| Unit cell dimensions | a = 7.1183(2) Å   alpha = 90 deg. |
| | b = 21.2160(7) Å   beta = 90 deg. |
| | c = 26.3602(9) Å   gamma = 90 deg. |
| Volume | 3981.0(2) Å$^3$ |
| Z, Calculated density | 8, 1.441 Mg/m$^3$ |
| Absorption coefficient | 4.283 mm$^{-1}$ |
| F(000) | 1776 |

TABLE 7-continued

Crystal Data of HCl salt: Form N-2

| | |
|---|---|
| Crystal size | 0.16 × 0.07 × 0.06 mm |
| Theta range for data collection | 2.67 to 44.53 deg. |
| Limiting indices | −6 <= h <= 5, −19 <= k <= 18, −23 <= l <= 23 |
| Reflections collected/unique | 9626/2985 [R(int) = 0.0700] |
| Completeness to theta = 44.53 | 95.3% |
| Data/restraints/parameters | 2985/0/505 |
| Goodness-of-fit on F^2 | 1.031 |
| Final R indices [I > 2sigma(I)] | R1 = 0.0580, wR2 = 0.1446 |
| R indices (all data) | R1 = 0.0780, wR2 = 0.1669 |
| Absolute structure parameter | 0.10(4) |
| Largest diff. peak and hole | 0.260 and −0.278 e. Å$^{-3}$ |

TABLE 8

Atomic Coordinates of HCl salt: Form N-2
Atomic coordinates (×10$^4$) and equivalent isotropic displacement parameters (Å$^2$ × 10$^3$) for Form N-2. U(eq) is defined as one third of the trace of the orthogonalized Uij tensor.

| | x | y | z | U(eq) |
|---|---|---|---|---|
| Cl(1) | 4498(5) | 2054(2) | 5726(1) | 84(1) |
| Cl(2) | 8606(6) | 2604(2) | 5897(1) | 98(1) |
| Cl(3) | 13423(5) | 8143(1) | 1794(1) | 75(1) |
| Cl(4) | 9097(4) | 8448(1) | 1988(1) | 73(1) |
| Cl(5) | −2074(4) | 5119(1) | 4228(1) | 71(1) |
| Cl(6) | 3031(4) | 5078(1) | 2983(1) | 66(1) |
| N(1) | 2223(11) | 4893(4) | 4125(3) | 52(2) |
| N(2) | 61(15) | 7409(6) | 6214(5) | 64(3) |
| N(3) | −573(13) | 7985(6) | 6078(5) | 65(3) |
| N(4) | −306(16) | 7936(6) | 6927(5) | 75(4) |
| N(5) | 7228(10) | 5382(4) | 3091(3) | 47(2) |
| N(6) | 9780(14) | 2724(5) | 1073(5) | 56(3) |
| N(7) | 10462(14) | 2158(6) | 1235(4) | 62(3) |
| N(8) | 10074(16) | 2166(6) | 367(4) | 70(3) |
| C(1) | 3750(20) | 3157(6) | 5294(4) | 67(4) |
| C(2) | 5220(20) | 2801(5) | 5526(4) | 62(4) |
| C(3) | 6990(20) | 3065(8) | 5577(5) | 75(4) |
| C(4) | 7330(20) | 3646(7) | 5390(5) | 75(5) |
| C(5) | 5980(20) | 3987(6) | 5149(5) | 67(4) |
| C(6) | 4180(20) | 3750(6) | 5092(4) | 57(4) |
| C(7) | 2634(17) | 4168(5) | 4848(4) | 53(3) |
| C(8) | 3267(15) | 4321(5) | 4307(4) | 54(3) |
| C(9) | 2762(18) | 5465(5) | 4424(5) | 63(4) |
| C(10) | 2298(13) | 5348(6) | 4977(5) | 44(3) |
| C(11) | 2294(14) | 4749(5) | 5175(5) | 42(3) |
| C(12) | 1796(17) | 4667(5) | 5682(5) | 57(3) |
| C(13) | 1424(16) | 5177(6) | 5975(5) | 57(3) |
| C(14) | 1510(15) | 5791(5) | 5785(5) | 45(3) |
| C(15) | 1928(14) | 5865(5) | 5284(5) | 44(3) |
| C(16) | 1095(14) | 6353(6) | 6107(5) | 44(3) |
| C(17) | 466(16) | 6920(7) | 5908(5) | 52(3) |
| C(18) | −747(19) | 8258(7) | 6533(8) | 79(5) |
| C(19) | 230(20) | 7382(8) | 6719(8) | 79(4) |
| C(20) | 856(16) | 6812(7) | 6955(5) | 61(3) |
| C(21) | 1241(15) | 6307(6) | 6639(6) | 58(4) |
| C(31) | 11260(20) | 6456(5) | 2095(6) | 68(4) |
| C(32) | 12471(16) | 6939(6) | 1978(4) | 63(4) |
| C(33) | 11878(19) | 7564(6) | 1953(6) | 61(3) |
| C(34) | 9939(18) | 7684(5) | 2033(4) | 55(3) |
| C(35) | 8744(17) | 7205(5) | 2162(4) | 51(3) |
| C(36) | 9370(18) | 6600(5) | 2199(5) | 52(3) |
| C(37) | 8002(17) | 6074(5) | 2356(4) | 49(3) |
| C(38) | 8399(14) | 5938(5) | 2920(4) | 51(3) |
| C(39) | 7870(18) | 4792(6) | 2834(5) | 60(4) |
| C(40) | 8081(17) | 4873(6) | 2263(5) | 53(3) |
| C(41) | 8178(17) | 5465(5) | 2060(5) | 52(3) |
| C(42) | 8419(18) | 5507(5) | 1536(6) | 66(4) |
| C(43) | 8611(16) | 4964(7) | 1238(5) | 59(3) |
| C(44) | 8532(18) | 4370(6) | 1459(5) | 54(3) |
| C(45) | 8220(15) | 4337(5) | 1978(5) | 57(3) |
| C(46) | 8796(17) | 3796(6) | 1143(5) | 54(3) |
| C(47) | 9454(15) | 3252(7) | 1367(5) | 56(3) |
| C(48) | 10601(16) | 1851(6) | 794(7) | 67(4) |

TABLE 8-continued

Atomic Coordinates of HCl salt: Form N-2
Atomic coordinates (×10$^4$) and equivalent isotropic displacement parameters (Å$^2$ × 10$^3$) for Form N-2. U(eq) is defined as one third of the trace of the orthogonalized Uij tensor.

| | x | y | z | U(eq) |
|---|---|---|---|---|
| C(49) | 9511(17) | 2725(6) | 563(7) | 55(4) |
| C(50) | 8909(16) | 3292(7) | 321(5) | 62(4) |
| C(51) | 8534(16) | 3805(6) | 614(6) | 53(3) |
| H(1A) | 2481 | 4958 | 3795 | 62 |
| H(1C) | 979 | 4827 | 4155 | 62 |
| H(5A) | 7327 | 5336 | 3429 | 56 |
| H(5C) | 6012 | 5453 | 3016 | 56 |
| H(1B) | 2535 | 2999 | 5277 | 81 |
| H(4B) | 8526 | 3818 | 5427 | 90 |
| H(5B) | 6262 | 4384 | 5021 | 80 |
| H(7B) | 1466 | 3924 | 4831 | 63 |
| H(8B) | 4609 | 4401 | 4302 | 65 |
| H(8C) | 3009 | 3966 | 4086 | 65 |
| H(9A) | 2075 | 5829 | 4301 | 76 |
| H(9B) | 4095 | 5547 | 4386 | 76 |
| H(12A) | 1718 | 4264 | 5818 | 68 |
| H(13A) | 1102 | 5116 | 6313 | 69 |
| H(15A) | 1967 | 6267 | 5145 | 52 |
| H(17A) | 322 | 6962 | 5559 | 62 |
| H(18A) | −1175 | 8671 | 6562 | 94 |
| H(20A) | 998 | 6783 | 7305 | 73 |
| H(21A) | 1607 | 5926 | 6783 | 70 |
| H(31A) | 11679 | 6042 | 2104 | 81 |
| H(32A) | 13726 | 6845 | 1914 | 76 |
| H(35A) | 7486 | 7294 | 2226 | 62 |
| H(37A) | 6713 | 6232 | 2322 | 59 |
| H(38A) | 9722 | 5846 | 2967 | 61 |
| H(38B) | 8090 | 6306 | 3123 | 61 |
| H(39A) | 6970 | 4458 | 2901 | 71 |
| H(39B) | 9067 | 4664 | 2976 | 71 |
| H(42A) | 8454 | 5901 | 1382 | 79 |
| H(43A) | 8793 | 5002 | 890 | 71 |
| H(45A) | 8104 | 3945 | 2133 | 69 |
| H(47A) | 9678 | 3241 | 1714 | 67 |
| H(48A) | 11041 | 1439 | 779 | 80 |
| H(50A) | 8777 | 3311 | −30 | 74 |
| H(51A) | 8094 | 4171 | 460 | 63 |

Example 11

Powder X-Ray Diffraction for Forms SA-1 and N-2

X-ray powder diffraction (PXRD) data were obtained using a Bruker C2 GADDS. The radiation was Cu Kα (40 KV, 40 MA). The sample-detector distance was 15 cm. Powder samples were placed in sealed glass capillaries of 1 mm or less in diameter; the capillary was rotated during data collection. Data were collected for 3≤2θ≤35° with a sample exposure time of at least 1000 seconds. The resulting two-dimensional diffraction arcs were integrated to create a traditional 1-dimensional PXRD. The results of the PXRD pattern and a simulated pattern calculated from the single crystal data for Form SA-1 are shown in FIG. 1.

Table 9 lists the characteristic PXRD peaks that describe Form SA-1 ((S)-7-([1,2,4]triazolo[1,5-a]pyridin-6-yl)-4-(3,4-dichlorophenyl)-1,2,3,4-tetrahydroisoquinoline monohydrochloride monoisopropanolate monohydrate) and Form N-2 ((S)-7-([1,2,4]triazolo[1,5-a]pyridin-6-yl)-4-(3,4-dichlorophenyl)-1,2,3,4-tetrahydroisoquinoline monohydrochloride). In particular, Table 9 shows characteristic diffraction peak positions (degrees 2θ±0.1) at room temperature, based on a high quality pattern collected with a diffractometer (cuKα) with a spinning capillary with 2θ calibrated with a NIST or other suitable standard.

TABLE 9

| Form SA-1 | Form N-2 |
|---|---|
| 5.8 | 8.3 |
| 8.1 | 8.9 |
| 9.1 | 10.9 |
| 10.8 | 14.2 |
| 11.7 | 14.7 |
| 13.0 | 16.7 |
| 13.3 | 17.3 |
| 14.5 | 18.0 |
| 15.1 | 18.4 |
| 15.4 | 18.8 |
| 16.2 | 20.2 |
| 16.8 | 21.9 |

Example 12

Differential Scanning Calorimetry for Form SA-1

Figure 2:
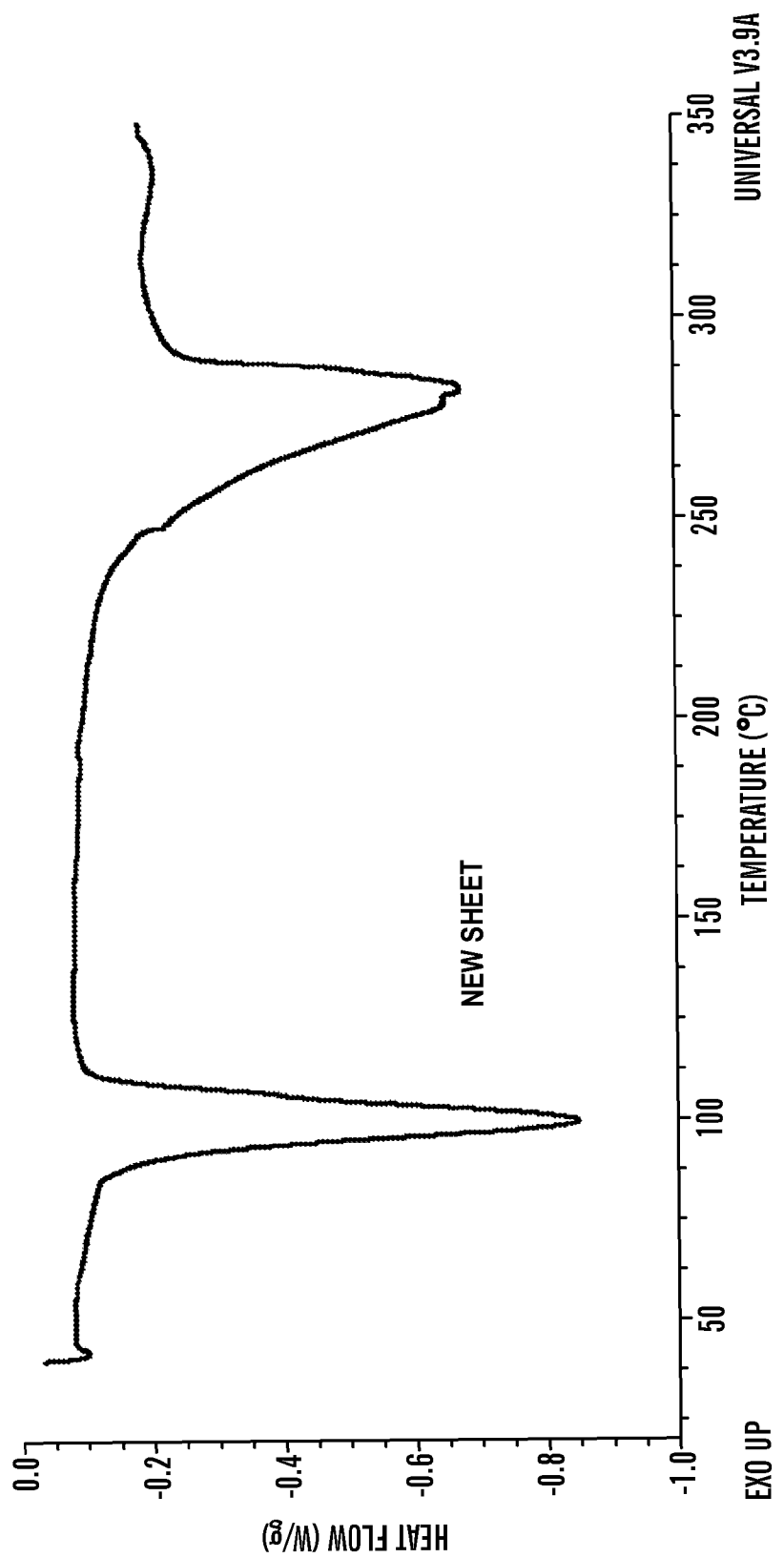
FIG. 2 illustrates the differential scanning calorimetry (DSC) pattern of Form SA-1.

Differential scanning calorimetry (DSC) experiments were performed in a TA Instruments™ model Q1000 or 2920. The sample (about 2-6 mg) was weighed in a pinpricked hermetically sealed aluminum pan and accurately recorded to a hundredth of a milligram, and transferred to the DSC. The instrument was purged with nitrogen gas at 50 mL/min. Data were collected between room temperature and 300° C. at 10° C.min. heating rate. The plot was made with the endothermic peaks pointing down. The results are shown in FIG. 2.

Example 13

Thermogravimetric Analysis for Form SA-1

Figure 3:
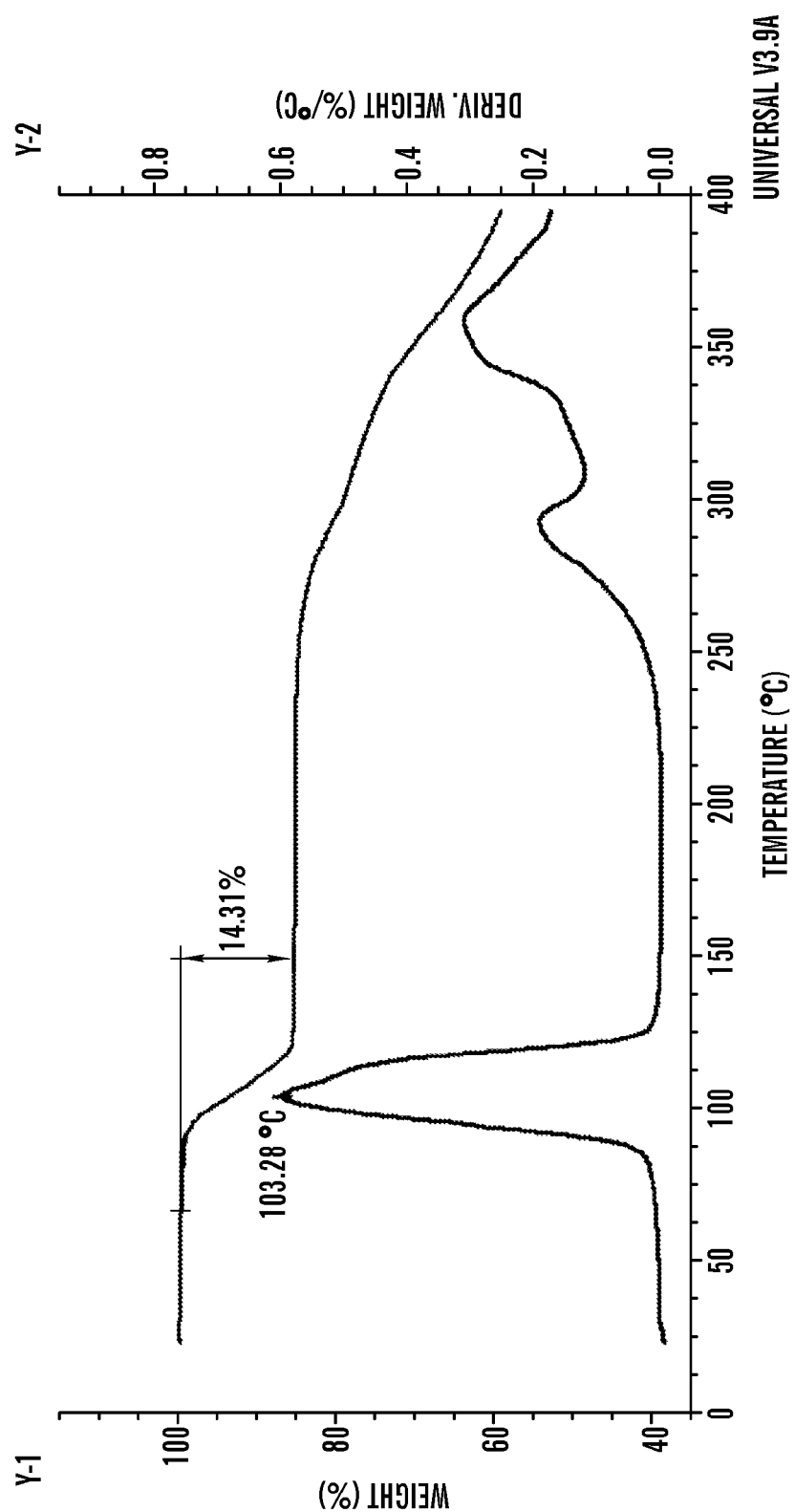
FIG. 3 illustrates thermogravimetric analysis (TGA) of Form SA-1.

The results are shown in FIG. 3.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of formula (I):

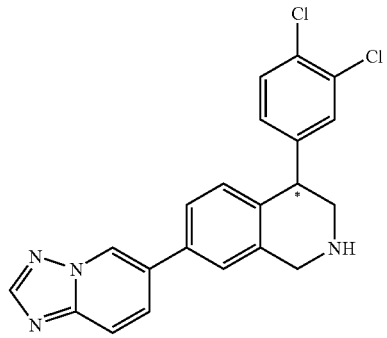

Formula I wherein:
the carbon atom designated * is in the R or S configuration; or a pharmaceutically acceptable salt thereof.

2. The compound according to claim 1, wherein the compound is a (+)-stereoisomer.

3. The compound according to claim 1, wherein the compound is a (−)-stereoisomer.

4. The compound according to claim 1, wherein the compound is in the S configuration.

5. The compound according to claim 1, wherein the compound is in the R configuration.

6. The compound according to claim 1, wherein the compound is a (S)(+)-stereoisomer.

7. The compound according to claim 1, wherein the compound is a (R)(−)-stereoisomer.

8. A pharmaceutical composition comprising a pharmaceutically acceptable carrier and a therapeutically effective amount of the compound according to claim 1.

* * * * *